(12) United States Patent
Lerner et al.

(10) Patent No.: US 6,626,670 B1
(45) Date of Patent: Sep. 30, 2003

(54) POWERED PERIOTOME

(75) Inventors: Sheldon Lerner, Cedarhurst, NY (US); Christopher Robert, 102 N. Franklin St., Lambertville, NJ (US) 08530; Anthony Handal, Westport, CT (US)

(73) Assignees: Sheldon A. Lerner, Cedarhurst, NY (US); Christopher Robert, Lambertville, NJ (US)

( * ) Notice: Subject to any disclaimer, the term of this patent is extended or adjusted under 35 U.S.C. 154(b) by 1 day.

(21) Appl. No.: 09/723,748

(22) Filed: Nov. 28, 2000

Related U.S. Application Data

(63) Continuation-in-part of application No. PCT/US00/30401, filed on Nov. 3, 2000.
(60) Provisional application No. 60/175,986, filed on Jan. 13, 2000.

(51) Int. Cl.⁷ .................................................. A61C 1/07
(52) U.S. Cl. ....................................... 433/122; 433/118
(58) Field of Search .................................. 433/118, 119, 433/120, 122, 124, 125

(56) References Cited

U.S. PATENT DOCUMENTS

| | | |
|---|---|---|
| 1,369,582 A | 2/1921 | Wagner |
| 1,503,610 A | 8/1924 | Smith |
| 1,605,320 A | 11/1926 | Bates |
| 1,605,322 A | 11/1926 | Bates |
| 1,875,680 A | 9/1932 | Van Horn |
| 2,552,134 A | 5/1951 | Berliner |
| 2,569,844 A | 10/1951 | Berliner |
| 3,325,900 A | 6/1967 | Sohlberg |
| 3,430,345 A | 3/1969 | Abreu |
| 3,555,685 A * | 1/1971 | Loge ........................... 433/102 |
| 4,060,897 A | 12/1977 | Greenstein |
| 4,259,069 A | 3/1981 | Lustig ......................... 433/144 |
| 4,270,902 A | 6/1981 | Wiland ........................ 433/144 |
| 4,608,019 A | 8/1986 | Kumabe et al. ............. 433/118 |
| 4,698,019 A | 10/1987 | Martin ......................... 433/144 |
| 4,854,867 A | 8/1989 | Meinershagen .............. 433/10 |
| 5,002,487 A * | 3/1991 | Tichy .......................... 15/22.1 |
| 5,024,600 A | 6/1991 | Kline ........................... 433/82 |
| 5,030,091 A | 7/1991 | Svanberg .................... 433/143 |
| 5,040,977 A * | 8/1991 | Weissman ................... 433/122 |
| 5,127,833 A | 7/1992 | Kline ........................... 433/143 |
| 5,169,313 A | 12/1992 | Kline ........................... 433/143 |
| 5,169,314 A | 12/1992 | Long ........................... 433/143 |
| 5,853,290 A * | 12/1998 | Winston ...................... 433/119 |
| 5,913,682 A | 6/1999 | Strate .......................... 433/143 |
| 5,924,864 A * | 7/1999 | Loge et al. .................. 433/112 |

FOREIGN PATENT DOCUMENTS

| | | |
|---|---|---|
| FR | 603190 | 4/1926 |
| WO | 8304175 | 12/1983 |

OTHER PUBLICATIONS

Satalec, Inc. USA, *TipBook*, Available at the 76th Annual Greater New York Dental Meeting on Nov. 26, 2000.
Satelec, Inc., *Suprasson P5 Booster*, Product Information card, Available at the 76th Annual Greater New York Dental Meeting on Nov. 26, 2000.

(List continued on next page.)

*Primary Examiner*—Cary O'Connor
(74) *Attorney, Agent, or Firm*—Handal & Morofsky

(57) ABSTRACT

A periodontal surgical instrument is disclosed which includes a motor. A rotary member is mounted for movement at a center of rotation of the rotary member. A shaft couples the output of the motor to the center of rotation of the rotary member. A coupling structure is secured to the rotary member at a point displaced from its center of rotation. A follower member is coupled to the coupling structure. A track member is coupled to the follower member and configured to allow the follower member to move in a closed loop path. A tool secured to the follower member. A method of use is also described for this periodontal surgical instrument for procedures where extraction is desired.

18 Claims, 26 Drawing Sheets

OTHER PUBLICATIONS

*A Supplement to The Compendium "Oral Hygiene"*, vol. 7, No. 4, distributed at the $76^{th}$ Annual Greater New York Dental Meeting on Nov. 26, 2000.

Bonart Medical Technology, Inc., *Piezoelectric Ultrasonic Scaler ART–PS,* Product information card. Available at the $76^{th}$ Annual Greater New York Dental Meeting on Nov. 26, 2000.

Bonart Medical Technology Inc., *Electrosurgery Unit ART–E1,* Product information card, Available at the $76^{th}$ Annual Greater New York Dental Meeting on Nov. 26, 2000.

Bonart Medical Technology Inc., *Magnetostrictive Ultrasonic Scaler ART–M1.* Product information card. Available at the $76^{th}$ Annual Greater New York Dental Meeting on Nov. 26, 2000.

Bonart Medical Technology Inc., *Combo Unit Piezo Scaler/Polisher ART–SP2.* Product Information card. Available at the $76^{th}$ Annual Greater New York Dental Meeting on Nov. 26, 2000.

Bonart Medical Technology Inc., *Combo Unit Magnet Scaler/Polisher ART–SP1,* Product Information card. Available at the $76^{th}$ Annual Greater New York Dental Meeting on Nov. 26, 2000.

* cited by examiner

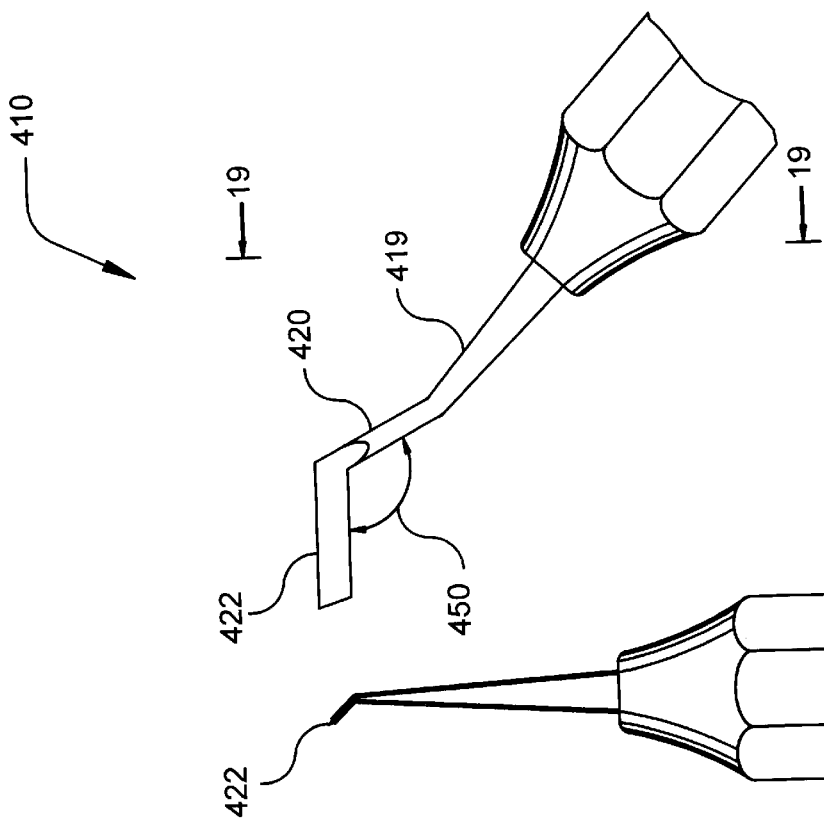
Figure 18
Figure 19
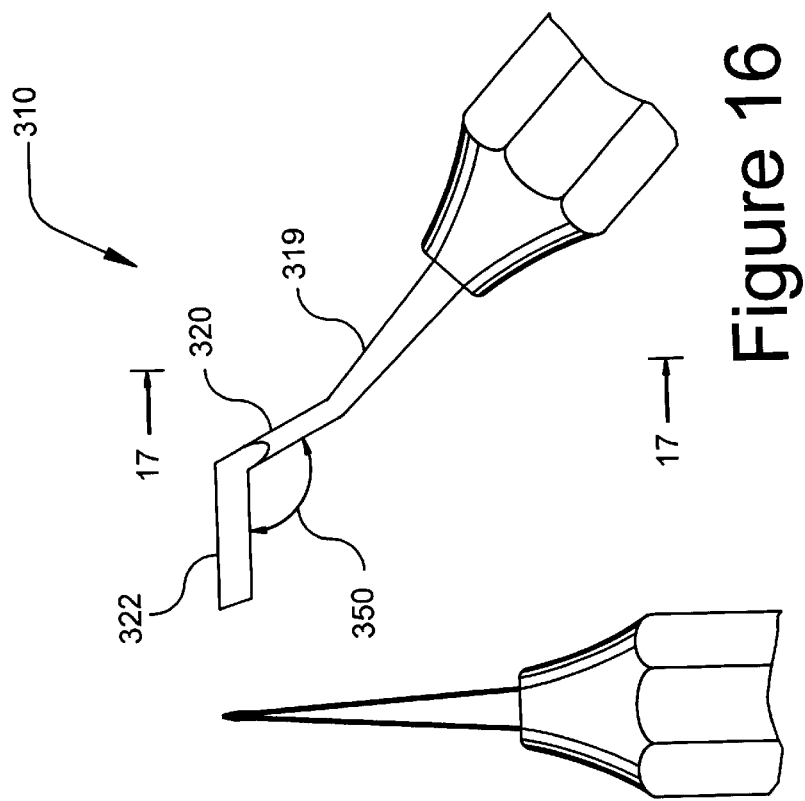
Figure 16
Figure 17

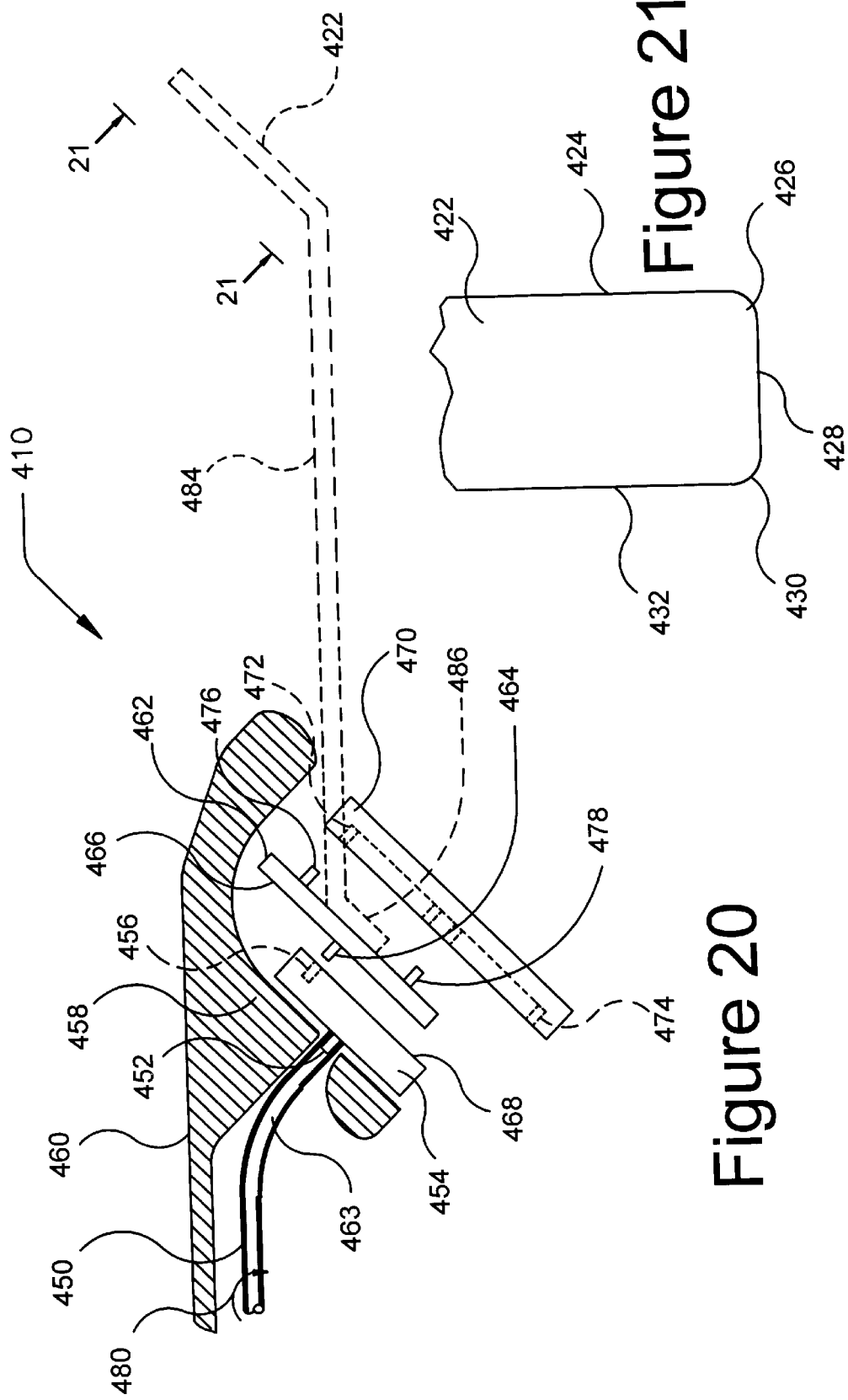

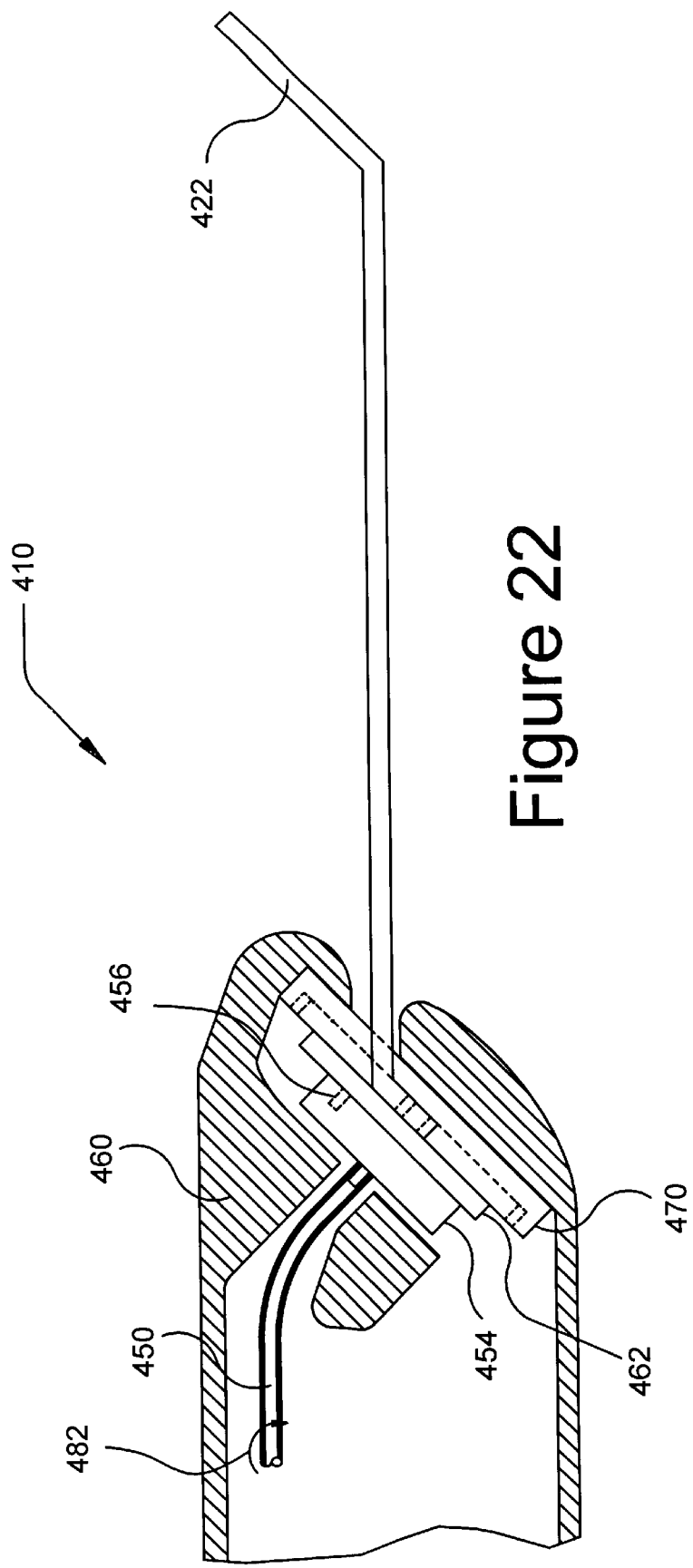

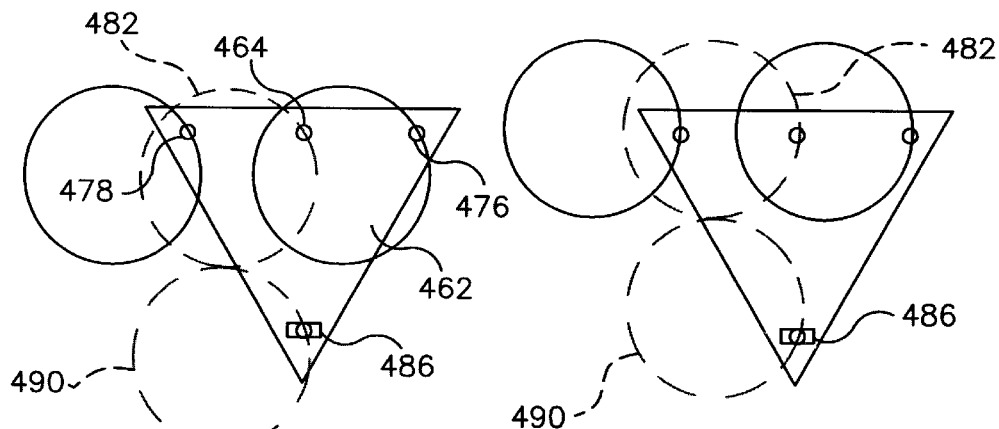
Figure 30
Figure 31
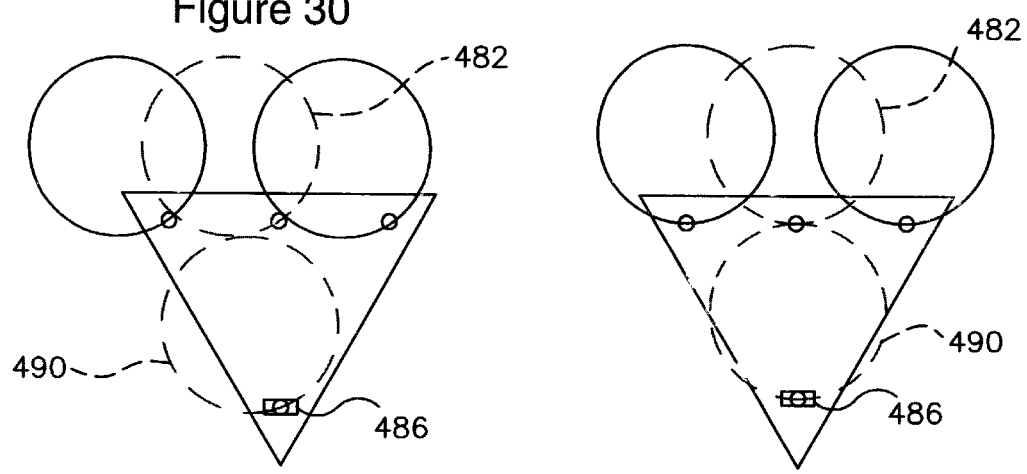
Figure 32
Figure 33
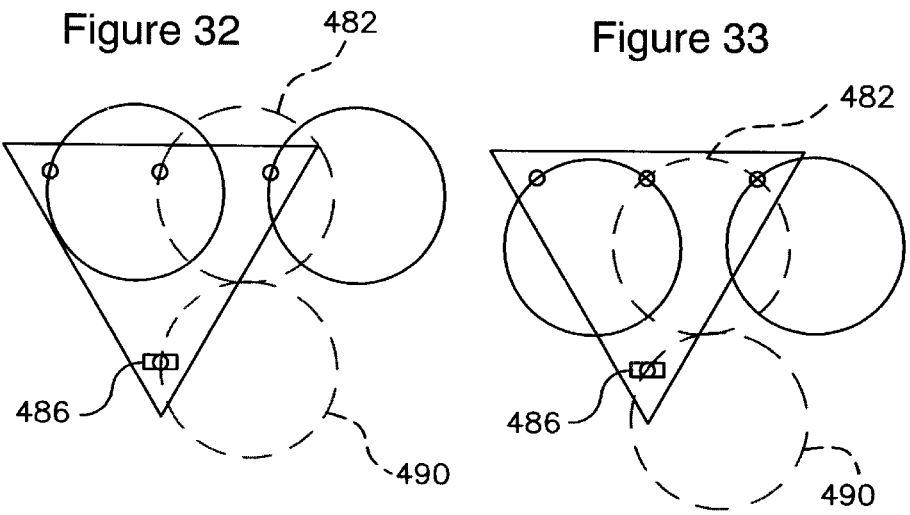
Figure 34
Figure 35

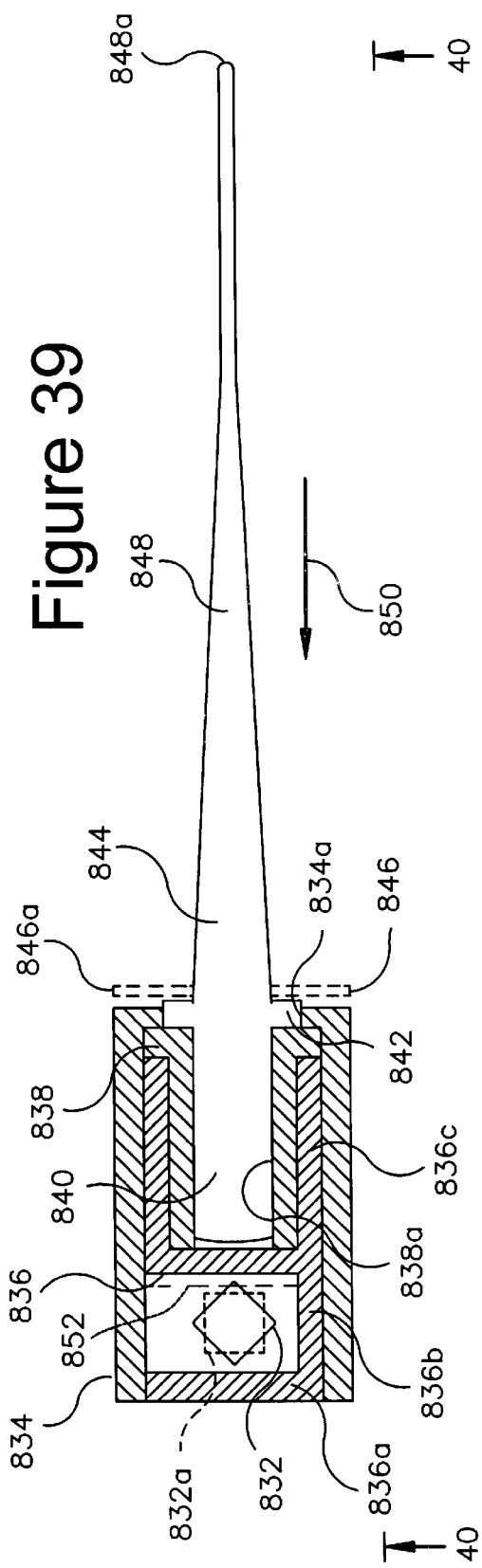

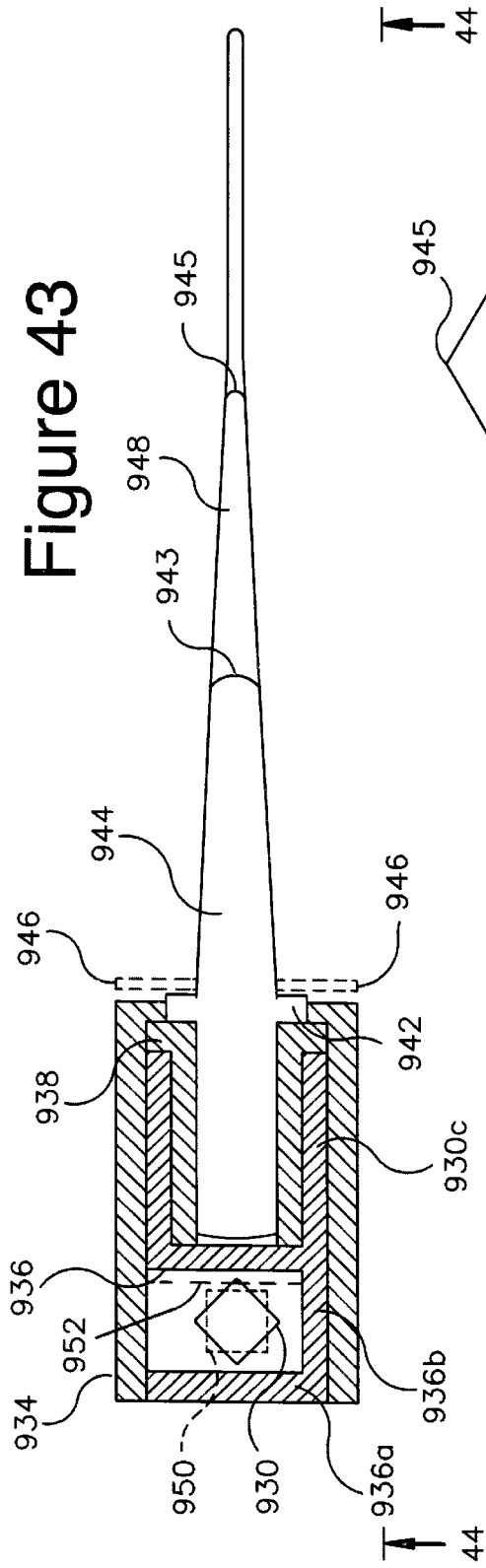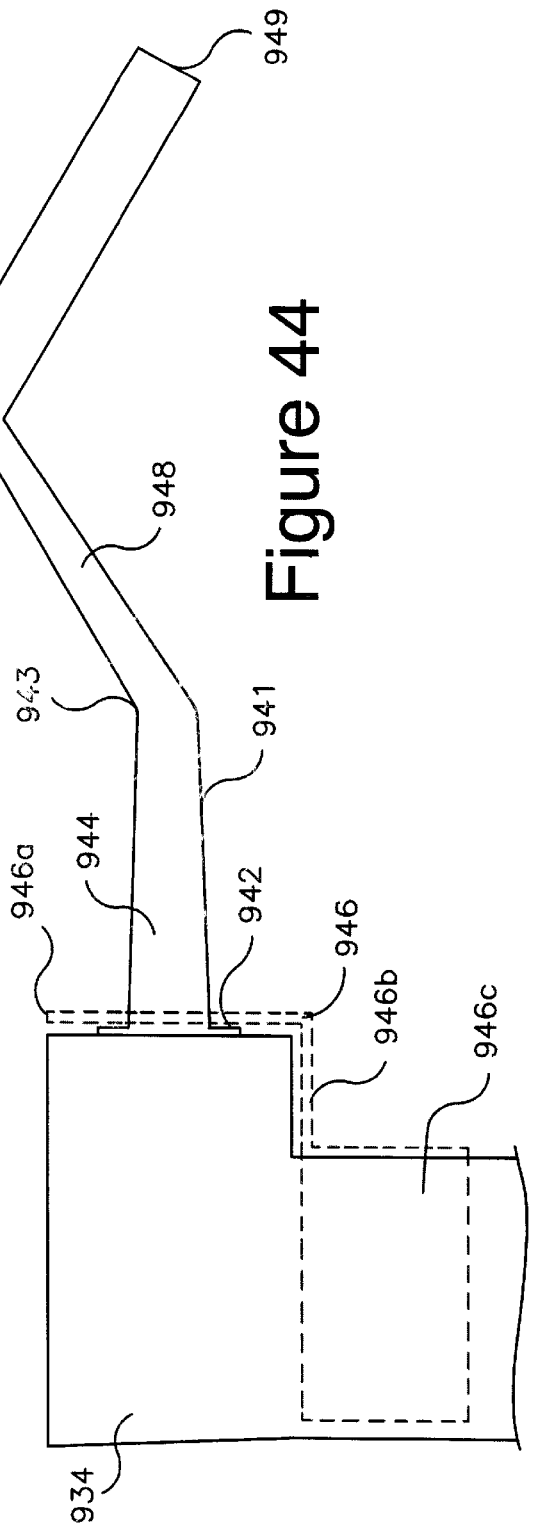

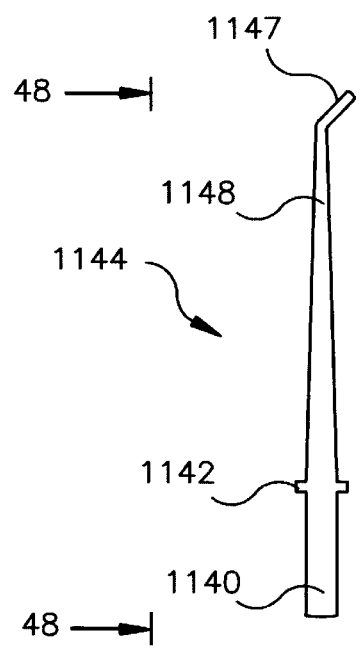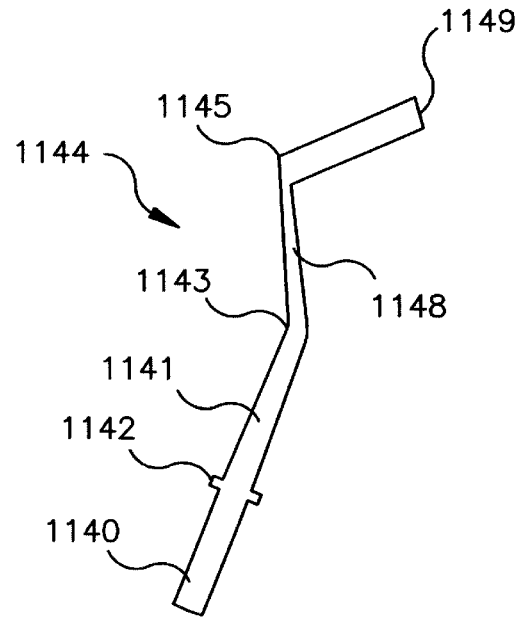# Figure 47  Figure 48
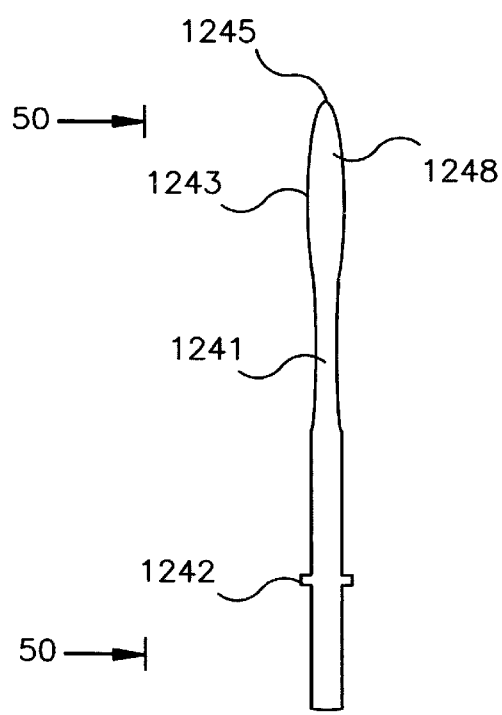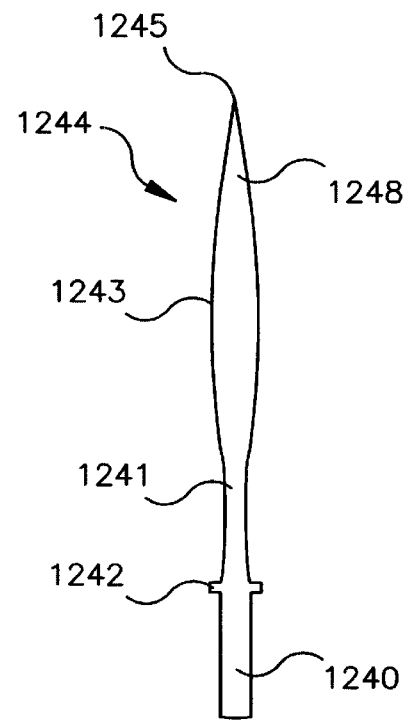# Figure 49  Figure 50

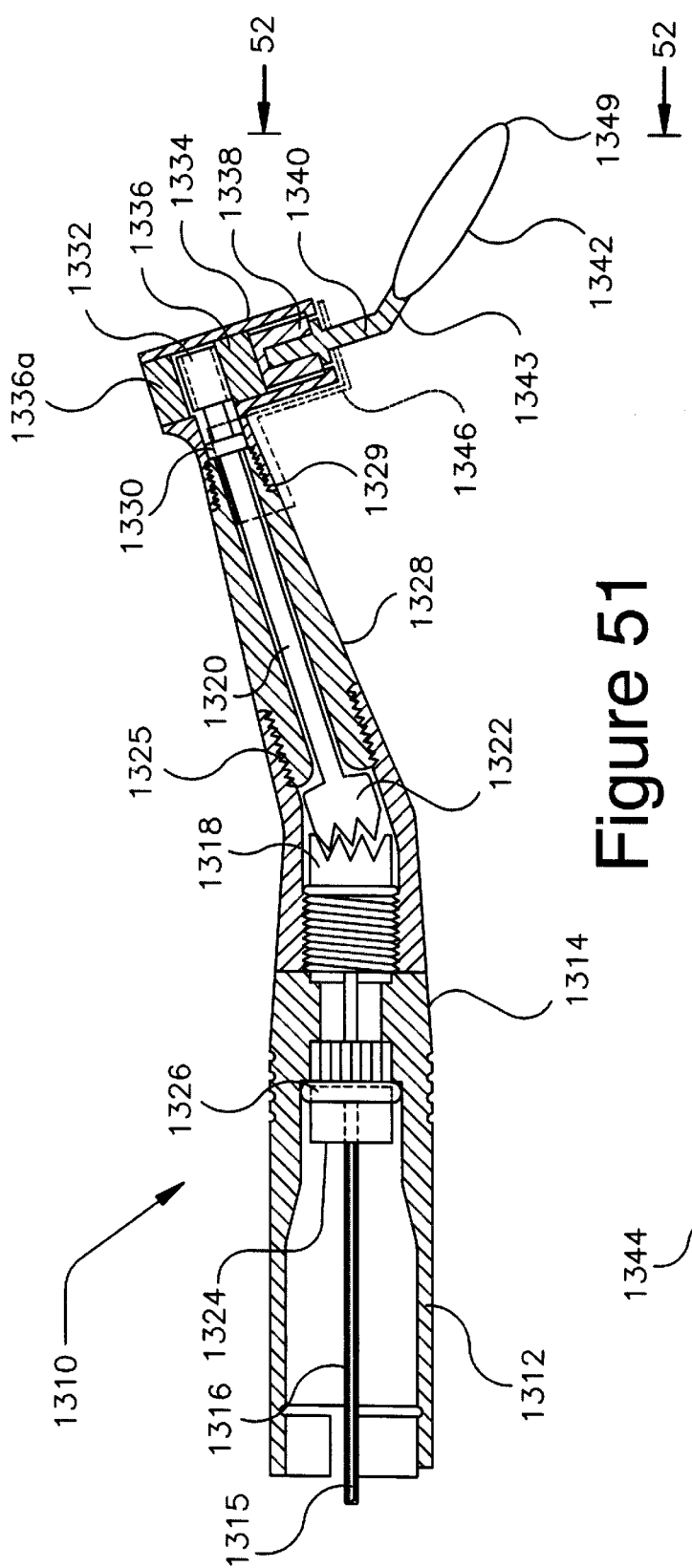
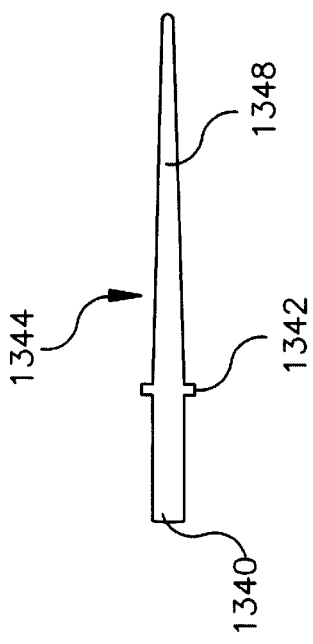
Figure 51
Figure 52

POWERED PERIOTOME

CROSS-REFERENCE TO RELATED APPLICATIONS

This application claims the benefit of provisional patent application No. 60/175,986, filed Jan. 13, 2000. In addition, this application is a continuation-part of international patent application number PCT/US00/30401 filed Nov. 3, 2000.

TECHNICAL FIELD

This invention relates to a motorized instrument and method for dental exodontia for the extraction of teeth. More specifically, the inventive instrument is designed to achieve the cutting of the fibrous attachment of the tooth to bone, formed of thousands of microscopic fibers, collectively referred to as the periodontal ligaments, or PDL.

BACKGROUND

Teeth generally comprise an upper exposed portion, or crown, which is visible and an underlying root structure which is hidden, being anchored within the bony substructure of the gums. The interface between the root structure of the tooth and the surrounding bone is a fibrous attachment. These fibers are referred to as the periodontal ligaments or PDL. The space occupied by the periodontal ligaments is known as the PDL space, and averages about 0.25 mm in thickness and surrounds the entire root structure of the tooth.

It is often necessary to separate the ligamental attachment during various surgical procedures. Such procedures include the extraction of teeth, and the installation of dental implants and common surgery to remove roots broken during extraction or through trauma. While extraction is one of the most common dental procedures it is fraught with difficulty. The great forces employed to dislodge teeth from bone are difficult to control and so, have unpredictable outcomes.

One of the main obstacles in the removal of teeth is to overcome the resistance of the PDL. The most common method used to overcome this resistance is bucco-lingual luxation, which expands the socket by loosening of the tooth by grasping with forceps and rocking the tooth in all directions in order to compress the proximate, relatively spongy portion of the surrounding bone, and stretch the periodontal ligaments until they break. Great force is needed to accomplish this, and the frequent result is fracture of the tooth or fracture of the surrounding bone that forms the buccal plate. Both of these problems lead to further surgical complications.

In the case of a fractured crown, it is often necessary to resort to a full-surgical extraction, elevating the soft tissue and removing bone, in order to gain access to the retained root. Full surgical procedures are time-consuming, traumatic to the patient, and carry more risk of infection and healing complications. In the case of a fractured buccal plate, the bone loses its blood supply, and will resorb away. Soft tissues will epithelialize faster than the bone will regenerate, and the remaining portion of the gum which formerly supported the tooth, also known as the ridge, will display a depression or defect. Loss of the bony architecture and its replacement by soft tissues, further complicates the prosthetic treatment plan. Indeed, in such a scenario, it is likely that a bone graft will be required. In other words, conventional crown and bridge prosthesis require bony support, and replacement of the tooth with an implant requires healthy surrounding bone. Often, it is necessary to do a separate preliminary surgery (Guided Bone Regeneration) to repair a defect before an implant is placed.

While instruments capable of cutting the PDL are known to be used in connection with the extraction of teeth, such instruments fail to have the range and configuration necessary to effectively perform this function. In addition, such prior art instruments are clumsy to work with and have limited functionality in connection with such cutting, because they are often too thick, or improperly angled.

SUMMARY OF THE INVENTION

It is an object of the invention to remedy the deficiencies of the prior art heretofore discussed.

It is a further object of the invention to provide an instrument which allows the separation of the ligamental attachment without destroying the buccal plate.

It is a further object of the invention to provide a motorized instrument with functional tools which function synergistically to allow the user to separate the ligamental attachment and allow teeth to escape the bone occlusally.

It is a further object of the invention to provide a method which allows the separation of the ligamental attachment while minimizing damage to the buccal plate.

The invention is directed to a dental instrument, namely a power periotome. The inventive instrument is of particular value because it comprises a handle having two tools. The handle is preferably made of hollow stainless steel, aluminum alloy or other lightweight material which makes it comfortable and easy to control. At one end there is a tool with a thin, flexible, angled blade for insertion to separate the gingival attachment and enter the PDL space. The angulation and length are suited to circumscribe the entire circumference of the root structure, all the way to the root apices.

At the other end of the inventive periotome there is a second tool which comprises a larger, spatula-shaped member tapering into a triangular tipped blade having a size and thickness adapted to create space for the introduction of extraction instruments in a controlled manner, after cutting out the PDL, and at locations dictated by the surgeon. The preservation of bone eliminates the need for follow-up repair of the ridge, simplifying the prosthetic treatment plan. In other words, the invention addresses the inefficiency of destroying the fibrous attachment by tearing apart the periodontal ligaments. Rather, in accordance with the invention, the ligaments are incised, with substantially no trauma to the surrounding bone.

In another aspect, the invention provides a motorized dental instrument comprising: a support member; a dental tool, said dental tool extending from said support member and being seated in said support member such that the dental tool is capable of linear motion; and, at least one mechanical link between the motor and said dental tool in said support member, whereby the dental tool is driven in reciprocating motion.

In a further aspect, the invention provides a motorized dental instrument, comprising: a support member; a dental tool, said dental tool extending from said support member and being seated in said support member such that the dental tool is capable of linear motion; a tappet seated in said support member, said tappet contacting said tool, whereby said contact extends said tool outward from said support member; at least one shaft rotatably seated in said support member, whereby said shaft is driven by said motor; and a cam coupled to said shaft, said shaft contacting said tappet.

In a still further aspect the invention provides a motorized dental instrument comprising: a support member; a dental tool, said dental tool extending from said support member and being seated in said support member such that the dental tool is capable of motion in a closed loop path; and, at least one mechanical link between the motor and said dental tool in said support member, whereby the dental tool is driven in reciprocating motion.

BRIEF DESCRIPTION OF THE DRAWINGS

Some embodiments of the invention will now be described in detail, by way of example, with reference to the accompanying drawings in which:

FIG. 16 is a side view of FIG. 15 across lines 16—16;

FIG. 17 is a perspective view of the scalpel or incisor tip being inserted into the PDL space on the buccal aspect of a maxillary right first molar;

FIG. 18 is a perspective view of the separator blade of the present invention being inserted into the PDL space on the mesial aspect of the same tooth;

FIG. 19 shows typical anatomy of a maxillary right first molar, surrounding bone and soft tissues, as viewed from the mesial aspect;

FIG. 20 is and exploded side view of a powered periotome constructed in accordance with the present invention;

FIG. 21 is a view of the blade of the powered periotome of FIG. 20;

FIG. 22 is a side view of a powered periotome constructed in accordance with the present invention;

FIGS. 30–35 are schematic diagrams illustrating the function of the track and follower in achieving the desired angularly fixed, circumferential movement in the powered periotome blade of the invention;

FIG. 39 is a detailed cross section view of the head housing illustrated in FIG. 36 viewed along lines 39—39.

FIG. 40 is a schematic side view of the head housing illustrating the retainer clip viewed along lines 40—40.

FIG. 43 is a detailed cross section view of the head housing similar to that of FIG. 39 illustrating an alternative tip embodiment.

FIG. 44 is a schematic side view of the head housing illustrated in FIG. 43 viewed along lines 44—44.

FIG. 47 is a top view of an alternative tip embodiment similar to FIG. 45, except with the head of the tip laterally flexed to the right.

FIG. 48 is a side view of the tip illustrated in FIG. 47 viewed along line 48—48.

FIG. 49 is a top view of an alternative tip embodiment.

FIG. 50 is a side view of the tip illustrated in FIG. 49 viewed along line 50—50.

FIG. 51 is a detailed schematic of the preferred embodiment of the power periotome with an alternative tip embodiment.

FIG. 52 is a side view of the tip illustrated in FIG. 51 viewed along line 52—52.

DETAILED DESCRIPTION OF THE PREFERRED EMBODIMENTS

Figure 1:
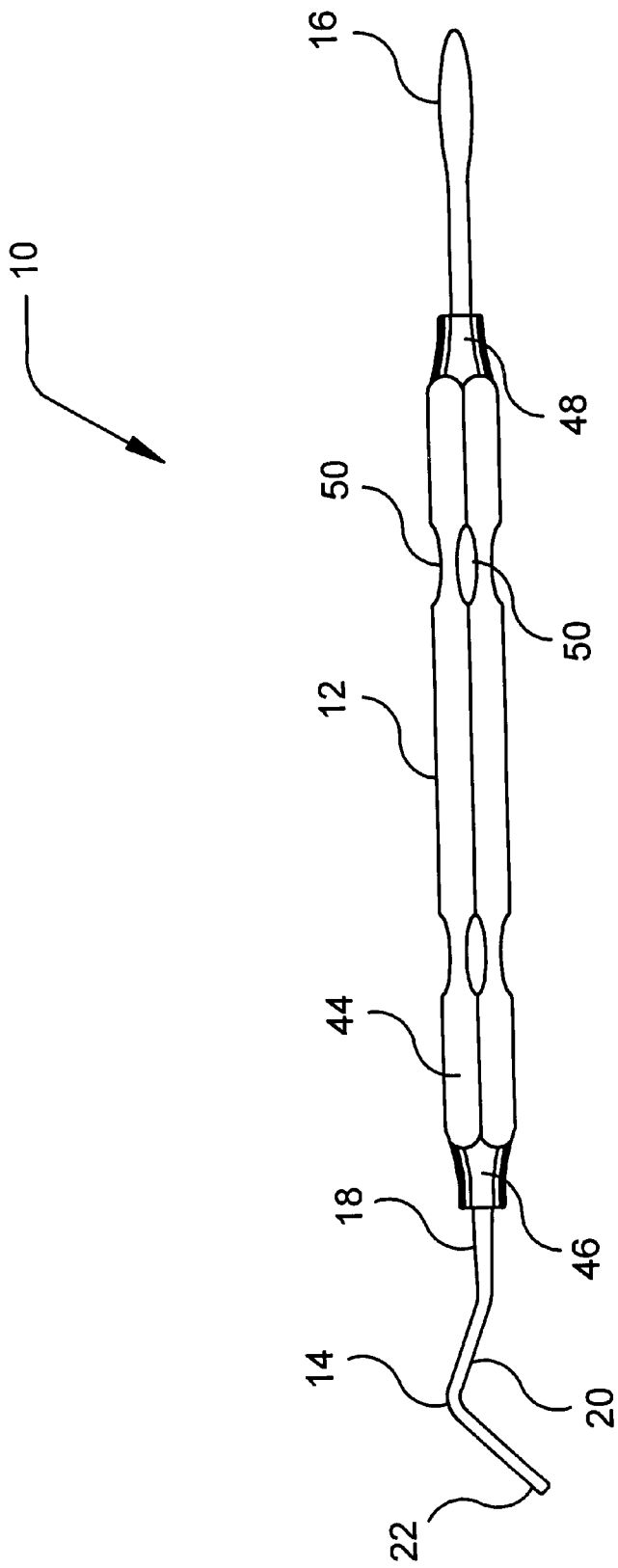
FIG. 1 is a side elevational view of a preferred embodiment of the invention.

FIG. 1 shows a preferred embodiment of the inventive periotome 10. Periotome 10 comprises a handle 12 with two functional tools 14 and 16 secured at each of its ends. In preferred embodiments, the cutting surfaces of the tools are coated with titanium nitride so that the blades remain sharp.

Figure 2:
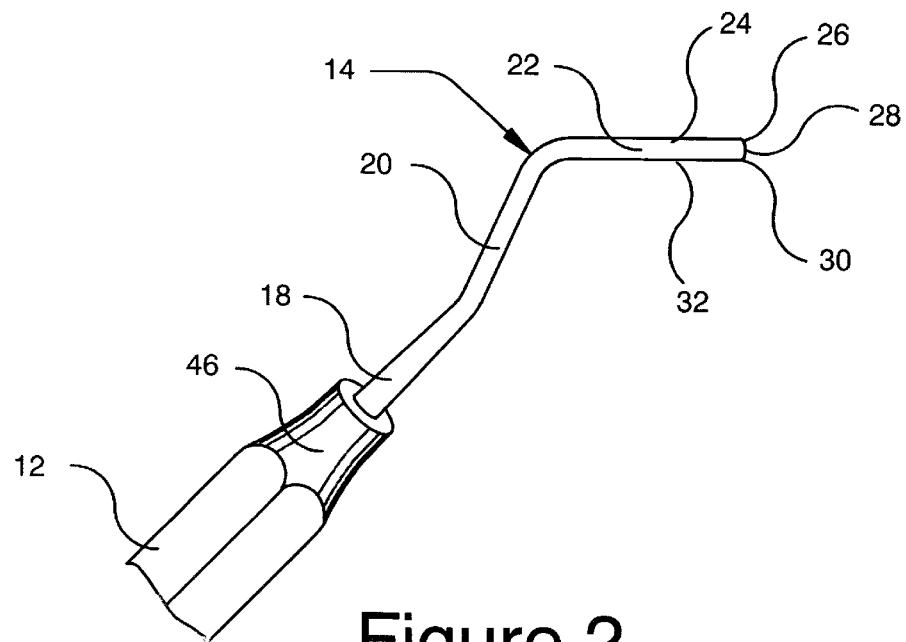
FIG. 2 is a detailed side view of a portion of the instrument shown in FIG. 1 showing the first tool.

As seen most clearly from FIG. 2, tool 14 preferably comprises three sections, a base 18, a stem 20, and a blade 22. Base 18, stem 20 and blade 22 are all formed from a single piece of metal. Base 18, stem 20 and blade 22 are connected at angles, preferably with rounded corners for safety. The angulation and length of the sections of tool 14 are suited to circumscribe the entire circumference of the root structure, all the way to the root apices.

Figure 3:
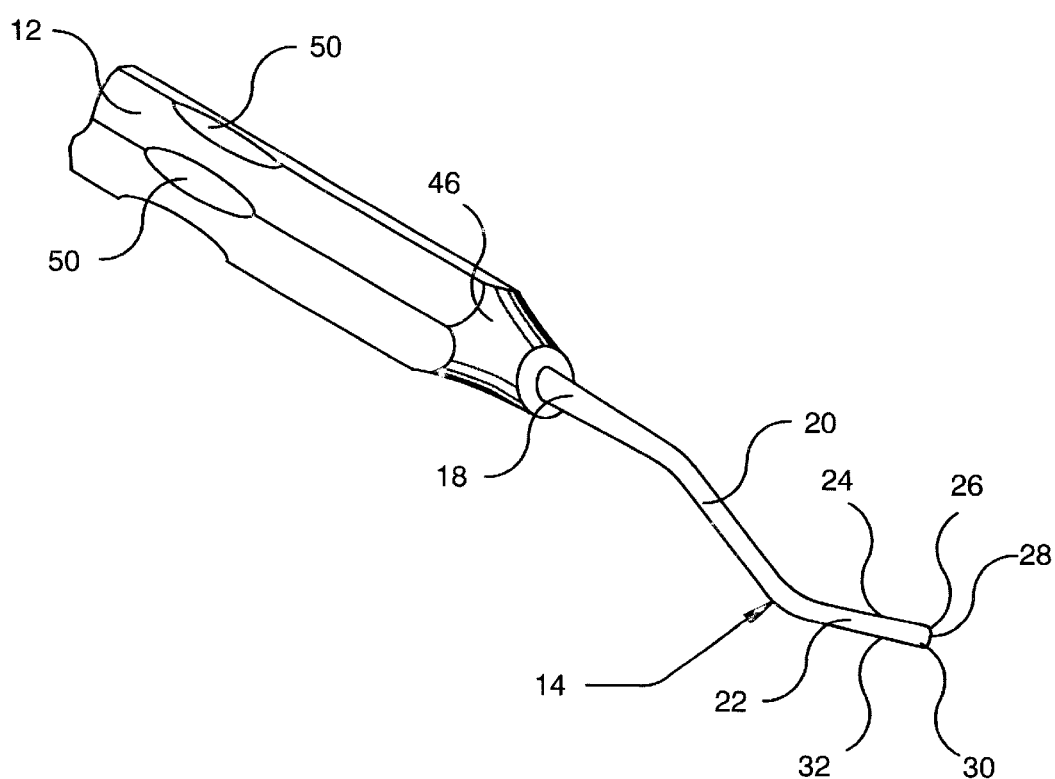
FIG. 3 is a detailed perspective view of a portion of the instrument shown in FIG. 1 showing the first tool.

Base 18 is formed as a roughly frustro conical member which tapers into stem 20. The length of base 18 is between 5–15 mm, preferably 10 mm. Its larger diameter adjacent handle 12 is 2.54 mm. Stem 20 is set at an angle of between 120–170 degrees, preferably 140 degrees in one direction from base 18. Stem 20 is formed as a continuing frustro conical member which tapers into blade 22. The length of stem 20 is between 5–15 mm, preferably about 8.9 mm while the larger diameter is between 1–2 mm, preferably about 1.5 mm. Blade 22 is set at an angle of between 20 and 45 preferably 39 degrees in the opposite direction with respect to stem 20. The sharp angle allows the user to get into a smaller area without hitting other teeth. Blade 22 is formed with a substantially rectangular shape and is flat with a thickness of about 0.46 mm, and a width of about 1.8 mm. Blade 22 preferably comprises a continuous cutting edge defined by five cutting surfaces 24, 26, 28, 30, and 32 as shown in FIGS. 2 and 3. Surfaces 24 and 32 are used to cut in the mesio-distal direction. Surface 28 is used to cut in the apical direction. Surfaces 26 and 30 are rounded points which can be used to cut in the apical direction.

Figure 4:
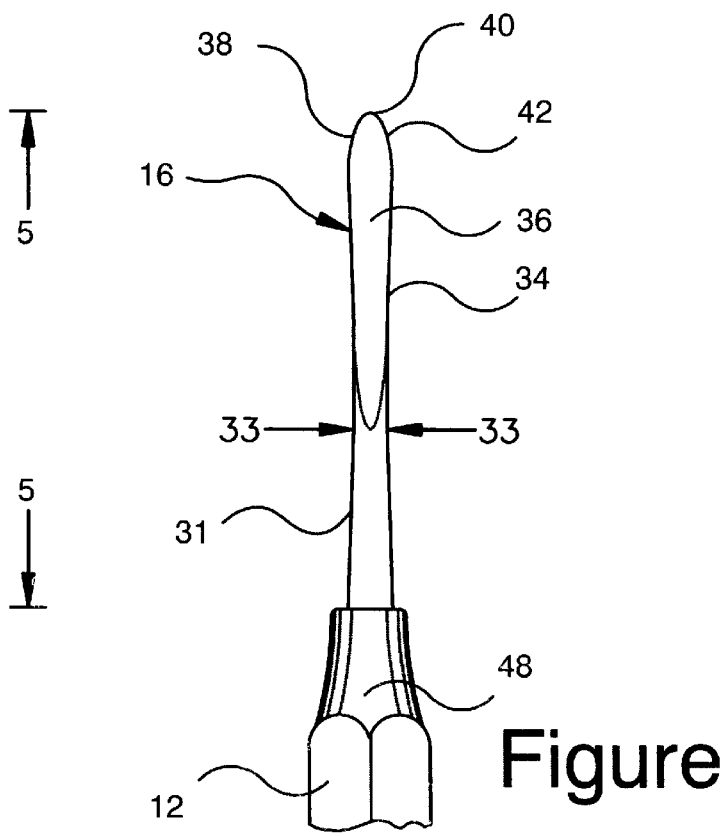
FIG. 4 is a detailed side elevational view of a portion of the instrument shown in FIG. 1 showing the second tool.

As shown in FIG. 4, tool 16 is formed from a member 34 which first tapers inwardly then outwardly into a spatula-shaped blade 36. In accordance with the preferred embodiment illustrated in FIG. 1, tool 16 has a length of about 25.4 mm. Member 34 has a thickness at point 31 of between 2–6 mm, preferably 3.30 mm in the direction of the plane of the drawing. It then tapers inwardly to a thickness of between 0.5–2.5 mm, preferably 1.9 mm at point 33 in the direction of the plane of the drawing of FIG. 4. Member 34 then flattens and expands to a width of between 2–6 mm, preferably 2.54 mm in the direction of the plane of the drawing. Member 34 preferably has a circular cross section point 31 and point 33.

Figure 5:
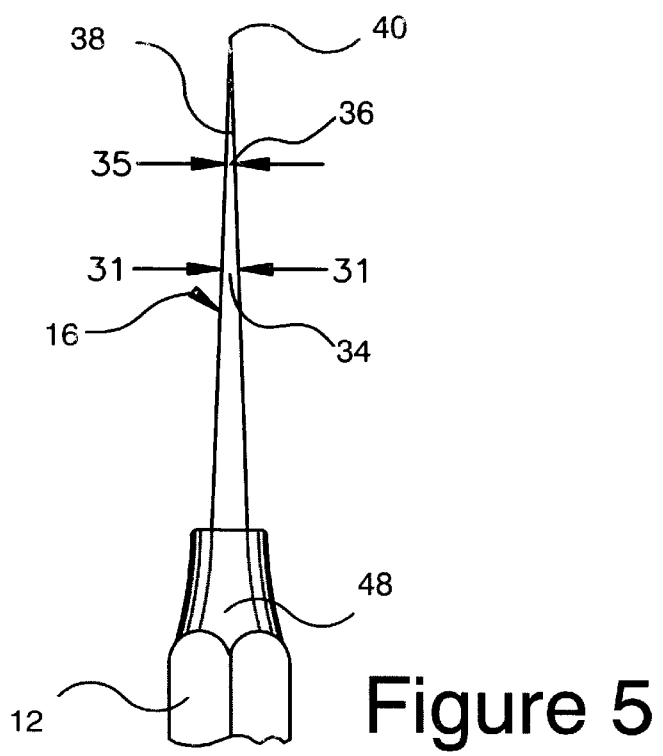
FIG. 5 is a detailed view along lines 5—5 of FIG. 4 showing other aspects of the configuration of the second tool.
Figure 6:
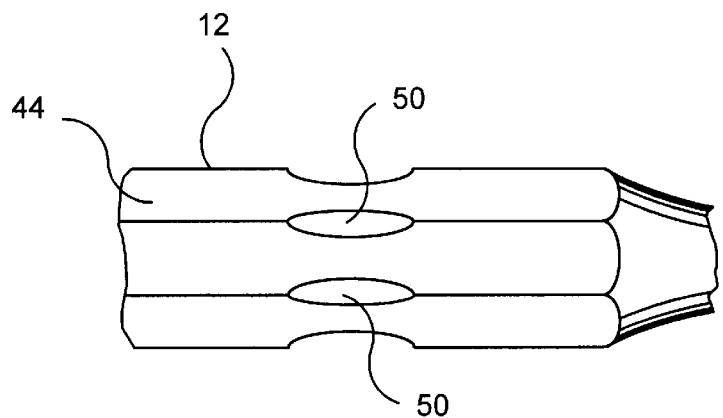
FIG. 6 is a detailed side view of the embodiment shown in FIG. 1 showing part of the handle.

FIG. 5 shows a side view of triangular tipped blade 36. Blade 36 is of a size and thickness so that the surgeon creates enough space for the introduction of extraction instruments in a controlled manner, and at locations dictated by the surgeon. More particularly, at point 35, the blade has a thickness on the order of between 1–3 mm, preferably 1.3 mm in the direction of the plane of the drawing of FIG. 5.

From there it terminates in a point. Blade 36 is preferably triangular in shape with three cutting surfaces, 38, 40, and 42. The length of blade 36 is about 37.4 mm. The angle of the tip is about 40 degrees.

Handle 12 is preferably made of hollow stainless steel. It is preferably lightweight, weighing about between 0.2 oz.–2.0 oz., preferably 0.8 oz. These parameters make handle 12 comfortable and easy to control. Handle 12 preferably comprises a center section 44 and two roughly frustro conical end sections 46 and 48. Center section 44 comprises a hollow tube which is formed for comfort to the user. In preferred embodiments, the tube has a triangular or hexagonal cross section so that the tool rests comfortably between the fingers. The length of center section 44 is between 60–120 mm, preferably 90 mm. Center section 44 has a diameter which is between 5–30 mm, preferably 11 mm. In preferred embodiments, center section 44 also comprises a plurality of support indentations or ridges 50 placed at points approximately ¼ and ¾ of the length of center section 44. The dimensions of the handle are balanced to reduce hand fatigue (where a larger diameter is preferred) with functionality as a dental instrument (where a smaller diameter is preferred). The larger diameter is available due to the angulation of tool 14 as the provision of at least three cutting surfaces on the tool to allow greater flexibility in smaller spaces as well the use of frustro conical tapered end sections 46 and 48.

Figure 7:
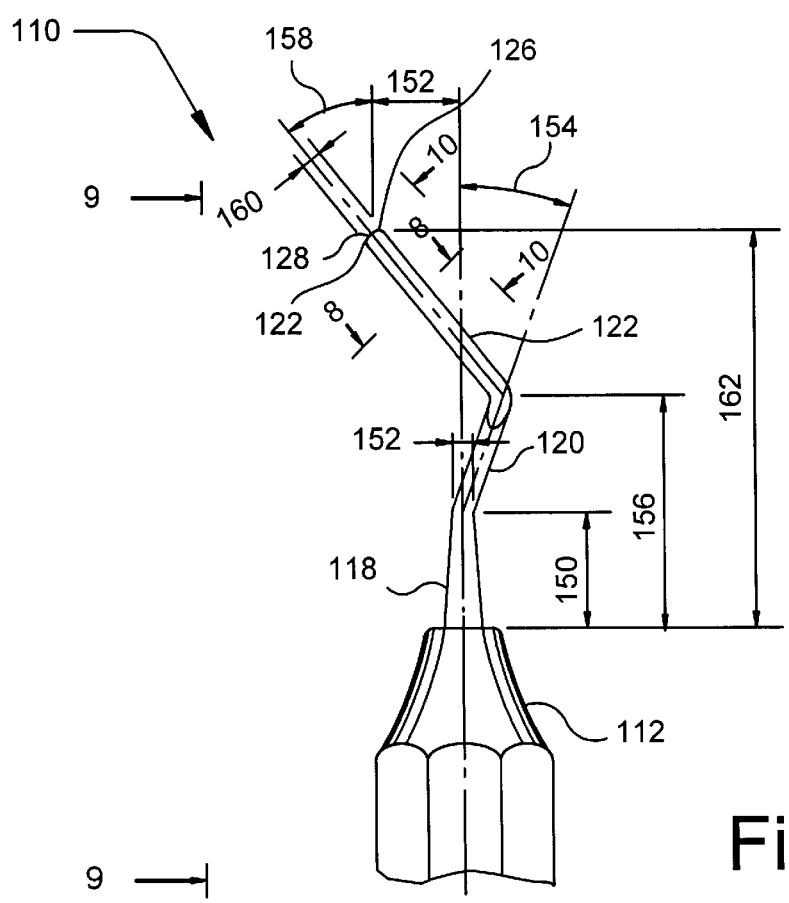
FIG. 7 is a front view of a portion of the instrument shown in FIG. 1 showing a second embodiment of the first tool.
Figure 8:
FIG. 8 is a side view of FIG. 7 across lines 8—8.
Figure 10:
FIG. 10 is a side view of FIG. 7 across lines 10—10.
Figure 9:
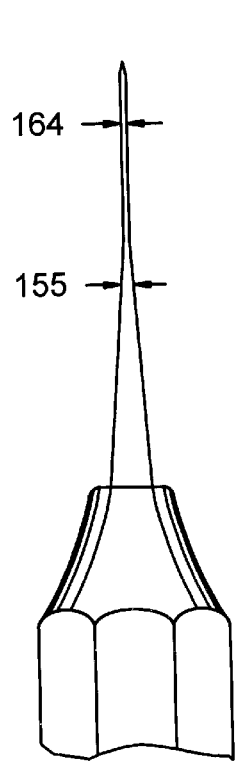
FIG. 9 is a side view of FIG. 7 across lines 9—9.

FIG. 7 shows a second preferred embodiment of the inventive periotome 110 which is similar in configuration to periotome 10. Base 118 is formed as a roughly frustro conical member which tapers into stem 120. The length 150 of base 118 is between 7 and 10 mm, preferably 8.6 mm. Diameter 152 is about 1.9 mm. Stem 120 is set at an angle 154 of about 20 degrees, from base 118. Stem 120 is formed as a continuing frustro conical member which tapers into blade 122. The length of stem 120 is preferably 16 mm while the larger diameter 155 is about 1.4 mm as shown in FIG. 9 which is a side view taken across lines 9—9 of FIG. 7. The vertical distance 156 from the top of stem 120 to the bottom of base 118 is about 17.35 mm. Blade 122 is set at an angle 158 of about 39 degrees from base 118 in the opposite direction. A side view of blade 122 across lines 8—8 is shown in FIG. 8. The length 160 of blade 128 is about 1.88 mm. The vertical distance 162 of blade 122 to base 112 is about 30 mm. The thickness 164 of blade 122 is about 5.3 mm. The shape between cutting surfaces 126 and 128 is a radius of about 0.031 inches. FIG. 10 is a side view across lines 10—10.

Figure 11:
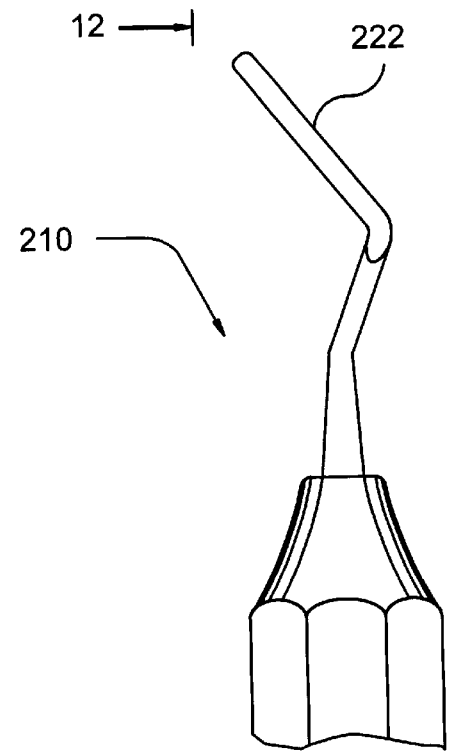
FIG. 11 is a front view of a portion of another embodiment of the inventive periotome.
Figure 12:
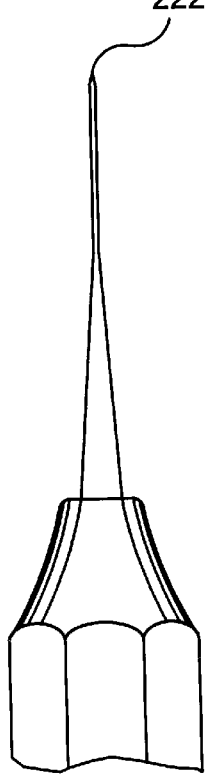
FIG. 12 is a side view of FIG. 7 across lines 12—12.

FIG. 11 shows another embodiment of the inventive periotome. Periotome 210 is similar in configuration to periotomes 10 and 110. However, blade 222 is now rotated between 20 to 80 degrees, ideally between 37 and 52 degrees, preferably about 45 degrees. The rotated blade allows the surgeon to come in from the front of the mouth and reach, for example, the interior portion of the back molars. FIG. 12 is a side view across lines 12—12. Without the angulation it is difficult for the surgeon to cut straight down into the gum line to separate the tooth because the cheek is in the way.

Figure 13:
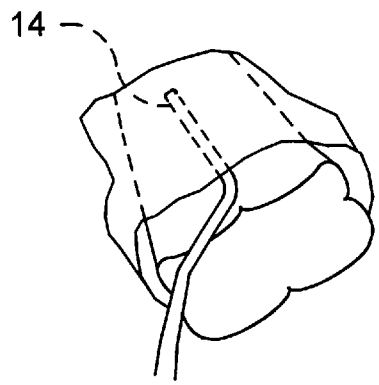
FIG. 13 is a front view of a portion of the instrument shown in FIG. 1 showing another embodiment of the first tool.
Figure 14:
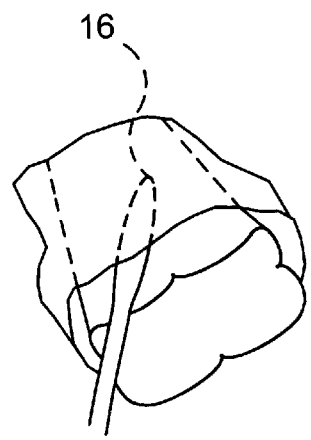
FIG. 14 is a side view of FIG. 13 across lines 14—14.

FIG. 13 shows a fourth preferred embodiment of the inventive periotome 310 which is similar in configuration to periotome 110. However, the angulation 350 of blade 322 from stems 319 and 320 is deeper. FIG. 14 is a side view taken along lines 14—14.

Figure 15:
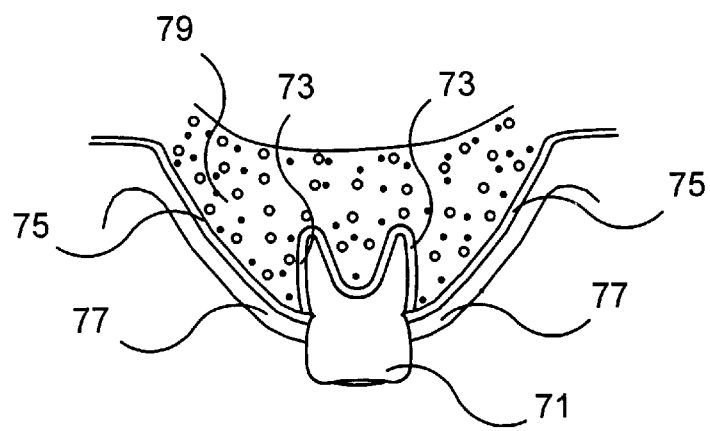
FIG. 15 is a front view of a portion of the instrument shown in FIG. 11 showing another embodiment of the first tool.
Figure 25:
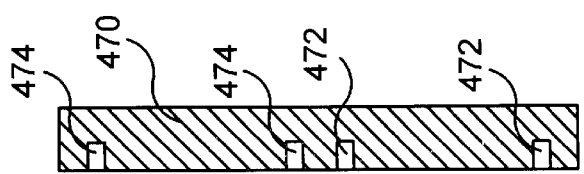
FIG. 25 is a view along lines 25—25 of FIG. 23, showing of the structure of the track member in cross-section.
Figure 26:
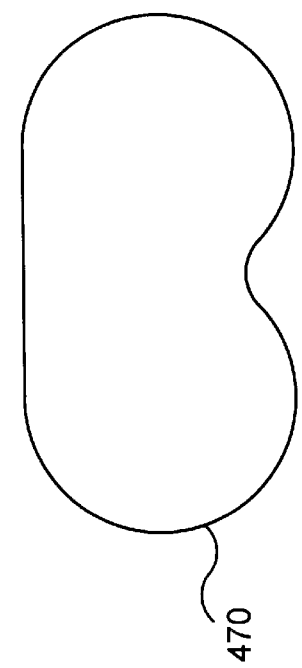
FIG. 26 is a view along lines 26—26 of FIG. 24, showing the back of the track member.
Figure 24:
FIG. 24 is a view along lines 24—24 of FIG. 23 showing the depth of the tracks in the track member.
Figure 23:
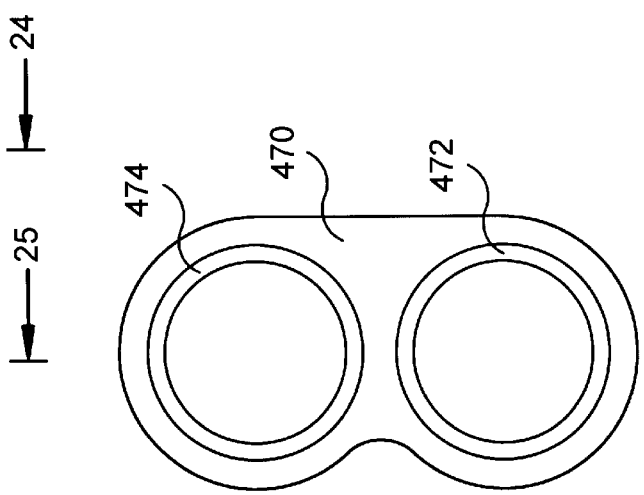
FIG. 23 is a plan view of a track member useful for converting rotary motion to angularly fixed circumferential motion.
Figure 27:
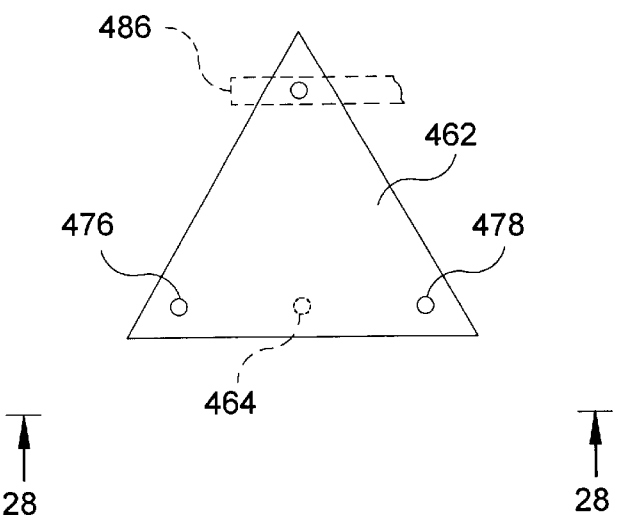
FIG. 27 is a plan view of a follower member useful in accordance with the method of the present invention.
Figure 28:
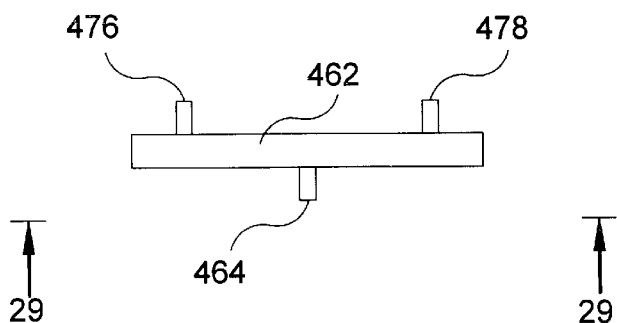
FIG. 28 is a view along lines 20a—20a a FIG. 27 showing a view of the follower member from the side.
Figure 29:
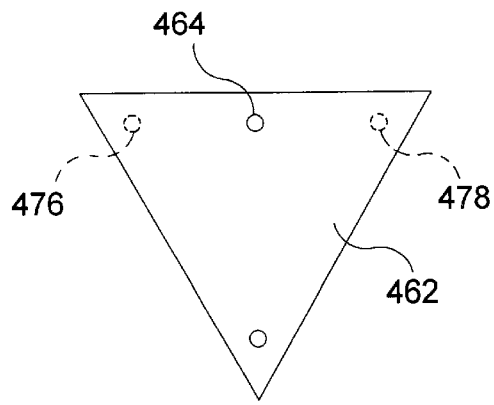
FIG. 29 is a detail along lines 29—29 of FIG. 28, showing a bottom plan view of the follower member of FIG. 27.

FIG. 15 shows a fifth embodiment of the inventive periotome 410 which is similar in configuration to periotome 310 with blade 422 rotated between 20 to 80 degrees, ideally between 37 and 52 degrees, preferably about 45 degrees. FIG. 15 is a side view taken along lines 15—15.

Although the above periotomes have been shown having a spatula shaped blade on one end, it is also contemplated that there may a surgical kit which comprises a periotome similar to that shown in FIG. 1 and a second periotome which comprises two angular blades similar to the blade shown in FIG. 11 but instead of having a spatula shaped tool on the second end, there may be instead a tool which is a mirror image of the first tool on the second end. It is also contemplated that the kit may comprise a handle with two ends and four tools mountable on at least one of the ends so that a surgeon would have all the tools necessary for cutting into the PDL space.

In practice, the surgeon will use tool 14 to come in from the occlusal direction and cut into the PDL space about 12 mm or so. The five cutting surfaces 24, 26, 28, 30, and 32 and flexibility of blade 22 allows the surgeon to come in from the side without hitting the jaw. Then the surgeon will gently insert triangular tipped blade 36 of tool 16 into the space made with tool 14. Then the surgeon will rock blade 36 back and forth so that cutting surfaces 38, 40, and 42 will gently expand the ridge of the socket with minimal compression to the bone without damaging the bone until there is enough space for the introduction of extraction instruments in a controlled manner, and at locations dictated by the surgeon. Normally, anatomy, i.e., proximity of other teeth, etc. dictates where elevators and forceps are applied. Here the site of application is formed by blade 36 where the surgeon can take advantage of greater bone mass. It is noted that the working tips of the instrument of the present invention are made of stainless steel. After being forged, the same are heat treated and sharpened. After being heat treated, tool 16 is formed into a specialized wedge to work as an adjunct to the cutting tip 14.

As can be seen in FIG. 13, the proper orientation of cutting tip 14 is substantially parallel to the axis of the tooth, allowing it to be advanced in the direction off the axis of the tooth into the periodontal ligament space on the buccal aspect of a maxillary right first molar. After tip 14 has been inserted into the space, it is carefully worked along the service on the tooth to create a space to allow tip 16 to be inserted as shown in FIG. 14. This is better understood with reference to FIG. 15 which shows typical anatomy of a maxillary right first molar, and surrounding bone and soft tissues, as viewed from the mesial aspect in cross-section. This anatomy includes the maxillary right first molar 71, the periodontal ligaments 73 completely surrounding the root structure and attaching it to bone, the cortical bone plate 75, and the gingival soft tissues 77. During use on the subject instrument, the objective is to cut as much of the periodontal ligaments 73 as possible, in order to treated to a more removal without destruction often be soft bone 79.

In accordance with a particularly preferred embodiment of the invention, structure is provided for increasing speed and control during the surgery. More particularly, when the periotome is being used to cut and separate tissue, careful angular and positional control of the cutting blade must be maintained while applying substantial force. Substantial improvement in use of the periotome is provided by the embodiment of the invention illustrated in FIGS. 20–35. More particularly, in accordance with this embodiment of the invention, the periotome incorporates a powered blade. Like the periotome illustrated in the previously described embodiment of the invention, the blade in the inventive powered periotome 410 illustrated schematically in FIG. 20 is substantially flat and exceedingly thin. Thus, the blade 422 generally lies in a plane perpendicular to the plane of the paper in FIG. 20.

In accordance with this embodiment of the invention, the blade is powered to have movement substantially only within the plane defined by the blade 422. In other words, referring to FIG. 21, which illustrates the blade 422 of the periotome illustrated in FIG. 20, during powered movement of the blade, the cutting edges 424, 426,428, 430 and 432 all move in one plane. Moreover, such movement is de minimis. However, such movement occurs very rapidly. For example, such movement may consist of elliptical or circular movement with sixty elliptical cycles occurring every second. The result is not to cut substantial amounts of tissue in any one cycle of the movement of the blade 422, but merely to make movement of the periotome relatively effortless and limited to guiding the cutting of the tissue by the powered scalpel cutting edge surfaces.

It is noted that if such movement is not in a plane, the result will be a flat periotome blade which has a cutting surface moving not only in the direction in which one wishes to cut tissue, but also moving with a component orthogonal to the desired direction of cutting, which can result in otherwise avoidable damage to tissues during the surgery.

In accordance with the invention, it is contemplated that movement of the periotome blade may be in one of three possible general modes.

In the first mode, such movement is in the plane of the blade of the periotome but only with a component perpendicular to small cutting surface 428 in FIG. 21. In this mode, the periotome is used in the powered mode strictly in a movement which involves insertion of the blade into and along the contour, which one wishes to cut, in the direction perpendicular to small cutting edge 428. As can be seen from the figures, cutting of tissue in the direction perpendicular to elongated cutting surfaces 424 and 432 in Figure will only be achieved in such mode in response to the manual application of force by the surgeon.

In the second mode, such movement is also in the plane of the blade of the periotome but only with a component perpendicular to the elongated cutting surfaces 424 and 432 in FIG. 21. In this mode, the periotome is used in the powered mode strictly in a movement in the direction perpendicular to elongated cutting edges 424 and 432. As can be seen from the figures, cutting of tissue in the direction perpendicular to the small cutting surface 428 in FIG. 21 will only be achieved in such mode only in response to the manual application of force by the surgeon.

In the third mode, such movement is again in the plane of the blade of the periotome but with both a component perpendicular to the elongated cutting edges 432 and 424, with a component perpendicular to small cutting edge 428 and with a component perpendicular to the rounded corner cutting edges 426 and 430. In this mode, the periotome is used in a very versatile movement which involves both insertion of the blade into and along the contour which one wishes to cut, in any direction, with the blade being moved to define the surface along which one wishes to cut. Moreover, such movement is achieved in such mode without the manual application of substantial force by the surgeon.

Referring to FIGS. 20 and 22, the operation of the powered periotome may be understood. A motor, not illustrated, is coupled to a flexible drive member 450 which, in turn, the secured to a drive stub 452 on a drive wheel 454. Drive wheel 454 includes a bore 456 position at a distance from the center of rotation of drive wheel 454. Drive wheel 454 is mounted for rotation in a bore 463 on a block 458. Block 458 is secured to and formed integral with the outer casing 460 of powered periotome 410.

Drive wheel 454 is, in turn, coupled to follower 462 which includes a follower pin 464 which is positioned within and mates with bore 456 in such a way that surface 466 bears against and slides against surface 468 when rotary drive is applied to flexible drive member 450.

Follower 462, in turn, rides within track member 470, which is illustrated in FIGS. 23–26. Track member 470 includes a pair of circular tracks 472–474. Tracks 472 and 474 mate with and receive follower pins 476 and 478. Track member 470 is secured in position within casing 460 as illustrated in FIG. 22 by glue. Alternatively, track member 470 may be formed integrally with casing 460.

When force is applied in the direction indicated by arrow 480 in FIG. 22, flexible drive member 450 rotates, resulting in rotation of drive wheel 454. This causes bore 456 to follow a circular path 482 displaced by a radius from the center of rotation of drive wheel 454. Because follower pins 476 and 478 are contained within circular tracks 472 and 474 engraved within track member 470, the result is that follower 462 maintains its angular position while moving along a circular path. This can be understood with reference to FIGS. 30 through 35.

As illustrated in FIG. 22, blade 422 is contained within a plane parallel to the plane which contains follower 462. Accordingly, because blade 422 is secured by shank 484 to a base 486 which is secured to follower member 462, as follower 462 moves, blade 422 also moves, but remains in one plane, thus achieving the desired cutting motion. More particularly, as rotary torque is applied to flexible drive member 450, a circular cutting motion is imparted to blade 422, while maintaining blade 422 in a single plane, thus achieving the operation defined as the third mode of movement above.

Such motion may be more clearly understood with reference to FIGS. 30 through 35. In particular, as follower 462 is moved, the result is that the base 486 is caused to move along a circular path 490, while maintaining a fixed angular orientation. More particularly, base 46, and blade 422 attached to it will in a circular path which is at the two o'clock position as illustrated in FIG. 30, the four o'clock position as illustrated in FIG. 31, the five o'clock position as illustrated in FIG. 32, the six o'clock position as illustrated in FIG. 33, the nine o'clock position as illustrated in FIG. 34, and finally the 11 o'clock position as illustrated in FIG. 35.

Figure 36:
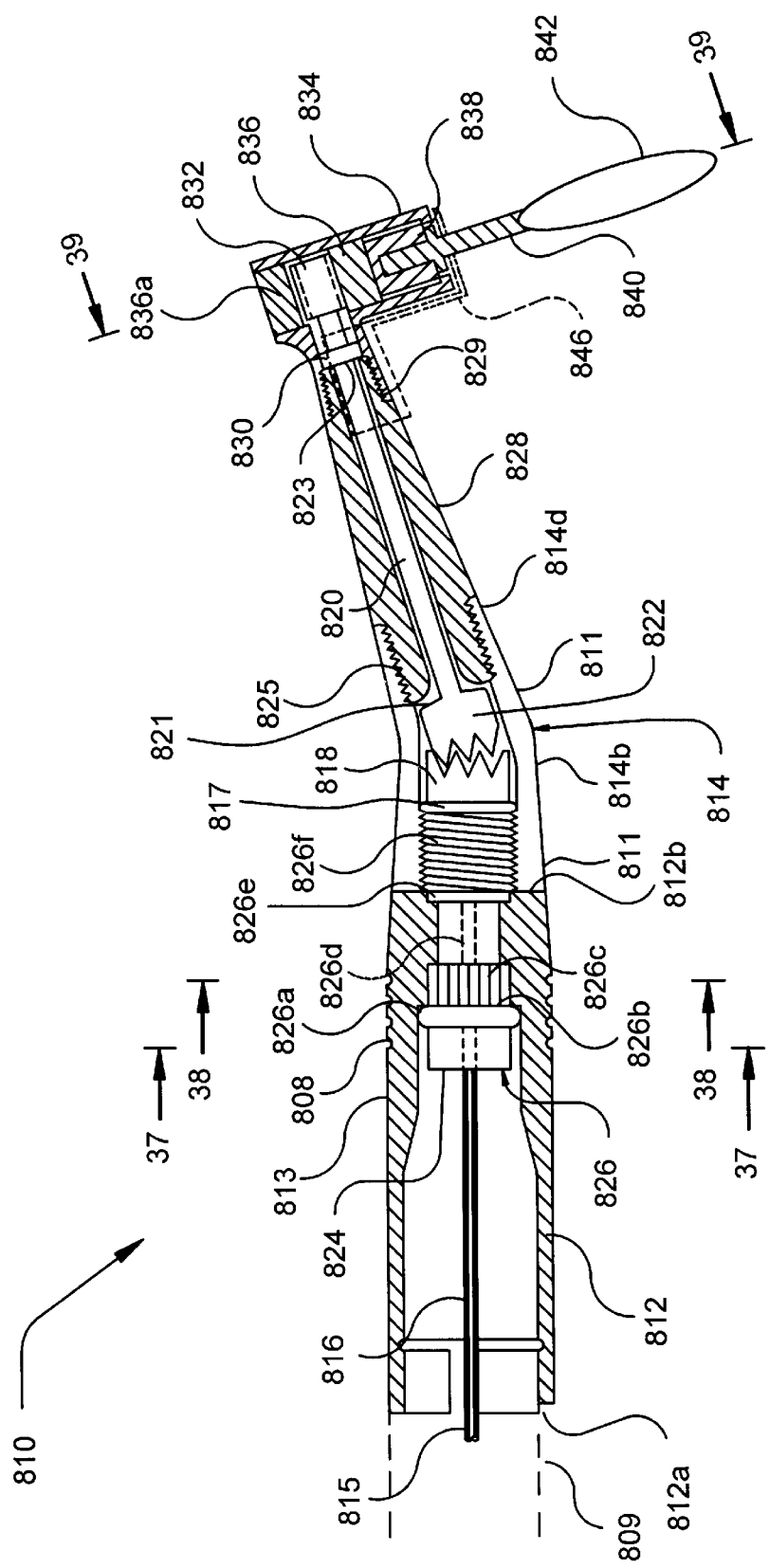
FIG. 36 is a detailed schematic of the preferred embodiment of the power periotome.
Figure 37:
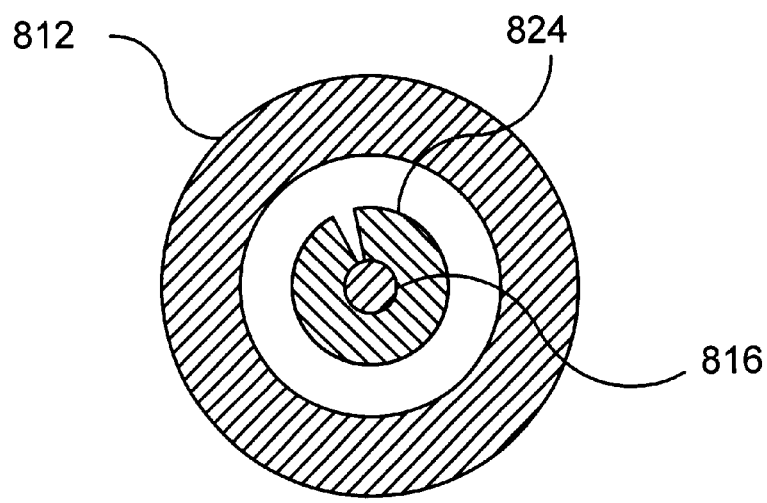
FIG. 37 is a cross section view of the compression band in the lower housing illustrated in FIG. 36 viewed along lines 37—37.

FIG. 36 illustrates inventive power periotome 810. Power periotome 810 comprises a housing 811. Housing 811 comprises a lower housing member 812 Lower housing member 812 attaches to a conventional power source 809, illustrated in phantom lines at an end 812a and an angled housing member 814 at an opposite end 812b of lower housing member 812. Serrations 808 are engraved in eight bands on outer surface 813 of lower housing member 812 to minimize slippage when power periotome 810 is being gripped by an operator Lower housing member 812 has a length of 33 millimeters and a diameter of ten millimeters. Contained within lower housing member 812 is a lower rotating rod 816. Lower rotating rod 816 has a height of 45 millimeters and a diameter of two millimeters and terminates within angled housing member 814 as a ten toothed crown gear 818. Gear 818 is three millimeters in height and five millimeters in diameter. Proximal end 815 of lower rotating rod 816 attaches to conventional power source 809. Gear 818 is mounted on distal end 817 of lower rotating rod 816. Gear 818 is housed in angled housing member 814. Gear 818 couples t6 a mating crown gear 822 which is secured to an upper rotating rod 820. A compression band 824 is attached to lower rotating rod 816 at a point 30 millimeters from proximal end 815 of lower rotating rod 816. Compression band 824 is one millimeter in thickness and two millimeters in height. Compression band 824 is compression fitted against lower rotating rod 816 and configured so as to prevent lower rotating rod 816 from slipping out of a ball bearing sleeve 826, as is illustrated in cross section in FIG. 37.

In connection with this invention, it is noted that all dimensions given are approximate and be widely varied.

Figure 38:
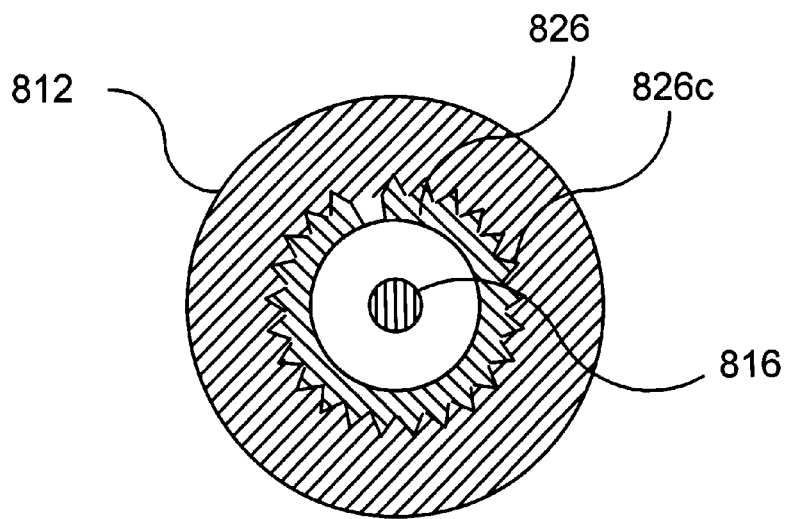
FIG. 38 is a cross section view of the ball bearing sleeve illustrated in FIG. 36 viewed along lines 38—38.
Figure 41:
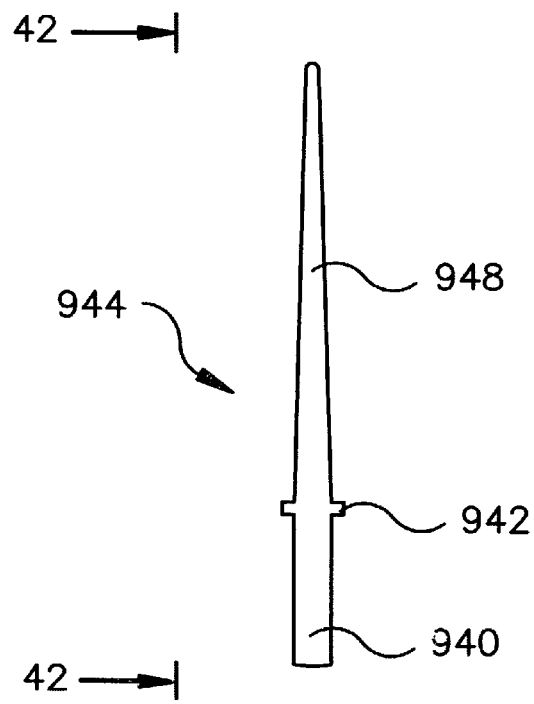
FIG. 41 is a top view of an alternative tip embodiment.

Just distal to compression band 824 is a ball bearing sleeve 826. Ball bearing sleeve 826 is thirteen millimeters in length; proximal end annular ridge 826a is one millimeter in height and six millimeters in diameter and configured to rest against compression band 824, moving distally the next half millimeter is an indentation 826b with a five millimeter diameter, the next distal two millimeters have longitudinal serrations 826c with an outside diameter of six millimeters. Longitudinal serrations 826c are so configured and dimensioned to be friction fitted with lower housing member 812, as is illustrated in cross section in FIG. 38. The next distal three and one half millimeters are smooth as indicated at area 826d with a diameter of six millimeters, the next distal one millimeter is indented as indicated at 826e to a diameter of five millimeters, terminating distally in a threaded region 826f of five millimeters in length and six millimeters in diameter. Threaded region 826f rests against a proximal surface 818a of gear 818. Threaded region 826f of ball bearing sleeve 826 provides a threaded attachment for lower housing member 812 with angled housing member 814.

Angled housing member 814 is bent at a seventeen degree angle rearward from a front (blade) surface 814a. A lower section 814b of angled housing member 814 is eight millimeters. Long Upper section 814d of angled housing member 814 is about seven millimeters. The intermeshing of gears 818 and gear 822 translates the rotation provided by conventional power source 809 to lower rotating rod 816 to upper rotating rod 820. Angled housing member 814 threadedly engages 825 upper housing member 828.

Upper housing member 828 contains upper rotating rod 820. Upper rotating rod 820 consists of mating gear 822 at a proximal end 821. Mating gear 822 is a ten toothed crown gear of three millimeters height and five millimeters diameter. A distal end 823 of upper rotating rod 820 has a cam base section 830, one millimeter in height and five millimeters in diameter, and a cam section 832 which is five millimeters in height and a two millimeter sided square with rounded edges. Upper housing member 828 engages a head housing member 834 via threads 829.

As demonstrated in FIG. 39 in a top view cross section, head housing member 834 contains cam section 832, cam follower 836, a blade coupling member 838, and a blade base post 840. Cam follower 836 contains a rear section 836a one millimeter thick and five millimeters in diameter, an arm section 836b, Arm section 836b connects rear section 836a with a front section 836c. Arm section 836b is three millimeters long and two millimeters thick, front section 836c is five millimeters long and five millimeters in diameter. Front section 836c is a hollow. As cam section 832 rotates to the position illustrated in phantom lines, cam follower 836 reciprocates within head housing member 834, with cam follower 836 moving posteriorly to dotted line 852 in response to applied pressure in the direction of 850 from a tooth being operated on.

Contained within hollow 836*d* of front section 836*c* is blade coupling member 838. Blade coupling member 838 has a hollow 838*a* to receive blade 848. Blade base post 840 is within hollow 838*a* of blade coupling member 838. Blade base post 840 is four millimeters in length and two millimeters in diameter. Blade ridge 842 fits into an anterior hollow 834a of head housing member 834. Retainer clip 846 secures blade 848 in position.

A retainer section 846*a* of retainer clip 846 is configured and dimensioned to match the anterior aspect of head housing member 834 with a one and one half millimeters section hollowed out in the center of the anterior aspect and a section in the top one and one half millimeters removed to allow for retainer clip 846 to be slipped in front of head housing member 834. The thickness of retainer clip 846 is three-tenths of a millimeter. An arm section 846*b* of retainer clip 846 travels posteriorly six millimeters to join with clip section 846*c*. Clip section 846*c* has a height of ten millimeters and sits on the anterior two-thirds of upper housing member 828, configured and dimensioned to approximate the diameter of the anterior two-thirds of upper housing member 828.

The preferred embodiment contains a straight blade 848 which is 30 millimeters in length, with a height tapering from three millimeters at blade ridge 842 to two millimeters at a point 20 millimeters from blade ridge 842 and then sustains the two millimeter height until a termination 848*a*. The distal end of blade 848 is rounded with a two millimeter width. The top view in FIG. 39 shows blade 848 tapering from three millimeters to one millimeter at a point 20 millimeters from blade ridge 842 and maintaining the one millimeter width through termination 848*a*. The distal ten millimeters of blade 848 has the superior, distal, and inferior surface honed to a sharp edges.

When it is desired to operate the inventive power periotome 810, the dentist or his assistant grabs the device after attaching it to a source of power 816 which is presently available in the offices of many dentist. When the power source is activated, rod 809 rotates, this results in rotating part 826. Because crown gear 817 is integral with part 826, mating crown gear 822 is caused to rotate. Result is that cam portion 832, which is rigidly secured to mating crown gear 822 is also caused to rotate. When the dentist presses blade 842 in position to sever the periodontal ligament, pressure is applied against blade 842 in the direction indicated by arrow 850 in FIG. 39. As cam portion 832 rotates, follower 836 is driven by the pressure in the direction of arrow 850 as cam 832 is driven from the position shown in solid lines in FIG. 39 to the position shown in phantom lines in FIG. 39. As cam 32 continues to rotate from the position shown in phantom lines to the position shown in solid lines, it drives follower surface 836 in the direction opposite the arrow 850 and thus imparting a reciprocating motion to blade 848.

Figure 42:
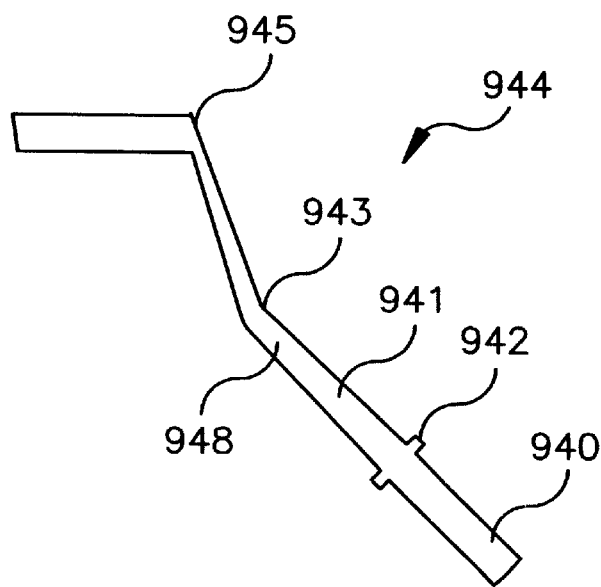
FIG. 42 is a side view of the tip in FIG. 41 viewed along lines 42—42.

FIGS. 41–44 illustrate an alternative tip embodiment. Corresponding parts have numbers 100 greater than corresponding parts in the embodiment illustrated in FIGS. 36–40. FIG. 43 shows a tip 944 within head housing member 934. Tip 944 is different from tip 844 by the use of an angled blade configuration. In particular, blade 948 is 27 millimeters in length with tapering from three millimeters at ridge 942 to one millimeter at a point seventeen millimeters from base ring 942. The distal ten millimeters of blade 948 maintains the one millimeter width with the superior, distal, and inferior surface honed to sharp edges. In FIGS. 42 and 44 it can be seen that blade 948 projects straight at portion 941 from base ring 942 a distance of ten millimeters, tapering from a height of three millimeters to two and one half millimeters. Blade 948 then takes a 25 degree superior turn 943 and extends for ten millimeters, further tapering from two and one half millimeters to two millimeters. Blade 948 then takes a 65 degree inferior turn 945 and extends for another ten millimeters, terminating with a two millimeter height rounded off at the tip 949.

FIGS. 45–48 illustrate a variation of the previous tip. Tip 1044 is similar to tip 944 except that the distal ten millimeters section is angled 45 degrees to the left at point 1047 in FIG. 45.

Tip 1144 is similar to tip 1044 except that the angle at point 1147 is to the right (FIG. 47).

Figure 45:
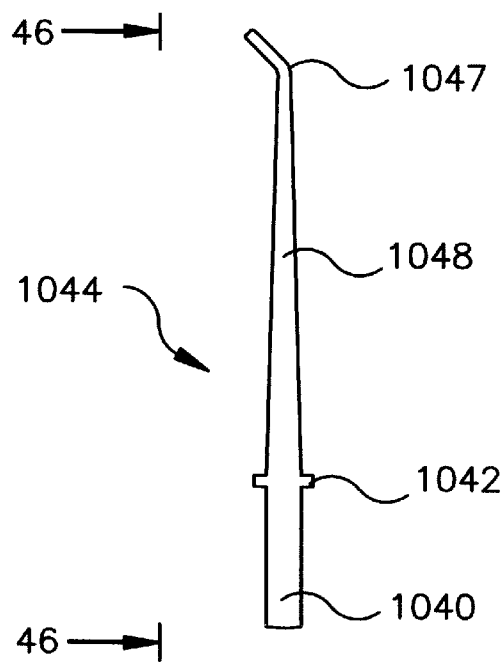
FIG. 45 is a top view of an alternative tip embodiment similar to that illustrated in FIG. 39 with the head of the tip laterally flexed to the left.
Figure 46:
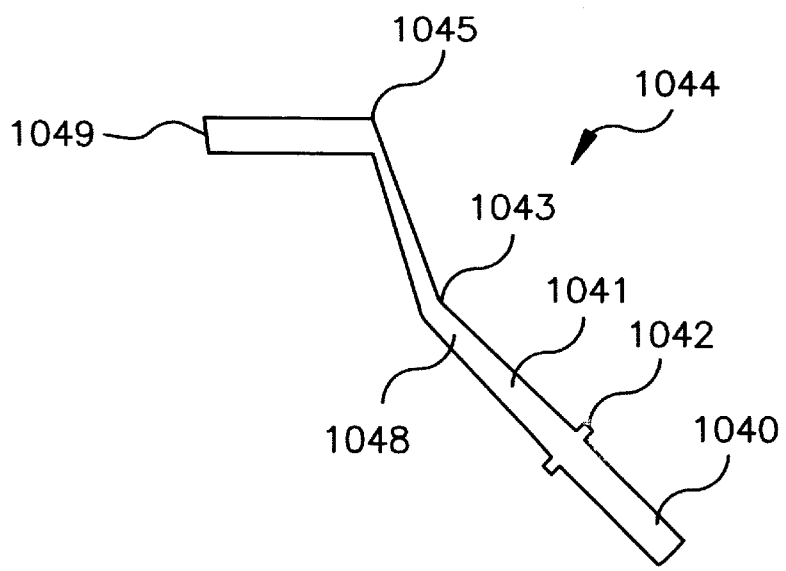
FIG. 46 is a side view of the tip in FIG. 45 viewed along lines 46—46.

The FIG. 45 and FIG. 47 tips allow the user to hug the surface of the tooth and root whether right or left, upper or lower.

FIGS. 49 and 50 illustrate another alternative tip embodiment. Blade base post 1240 is four millimeters in length and two millimeters in diameter. Blade ridge 1242 is one millimeter in length and three millimeters in diameter. In side view, as illustrated in FIG. 49, blade 1248 projects distally 38 millimeters. At blade ridge 1242 the diameter of blade 1248 is three millimeters and tapers to two millimeters at a point 1241 ten millimeters from blade ridge 1242, for the next distal twenty millimeters blade 1248 widens 1243 to three millimeters with the terminal eight millimeters tapering to a point 1245. The top view illustrated in FIG. 50 shows at blade ridge 1242 the diameter of blade 1248 three millimeters and tapers to two millimeters at a point ten millimeters from blade ridge 1242, in the next distal ten millimeters blade 1248 widens to three millimeters and the terminal 18 millimeters tapers to a point.

FIGS. 51 and 52 illustrate another alternative tip embodiment. Similar to the previous embodiments, housing member 1314 threadedly engages 1325 upper housing member 1328. Blade base post 1340 is four millimeters in length and two millimeters in diameter. Blade ridge 1332 is one millimeter in length and three millimeters in diameter. Distal to blade ridge 1342 straight blade 1348 which is 30 millimeters in length, angles superiorly 40 degrees at a point 1343 twenty millimeters from blade ridge 1342 to approximate the angle of the non-powered handtool currently in use. Blade 1348 has a length of 30 millimeters from blade ridge 1332. The present embodiment has a height of three millimeters from blade ridge 842 to its termination. Distal end 1349 of blade 1348 height is rounded with a two millimeters width. The top view of tip 1344 only (FIG. 52) shows blade 1348 tapering from three millimeters to one millimeter at 20 millimeters from blade ridge 1342 and maintaining the one millimeter width through the termination of blade 1348. The distal ten millimeters of blade 1348 has the superior, distal, and inferior surface honed to sharp edges.

Figure 53:
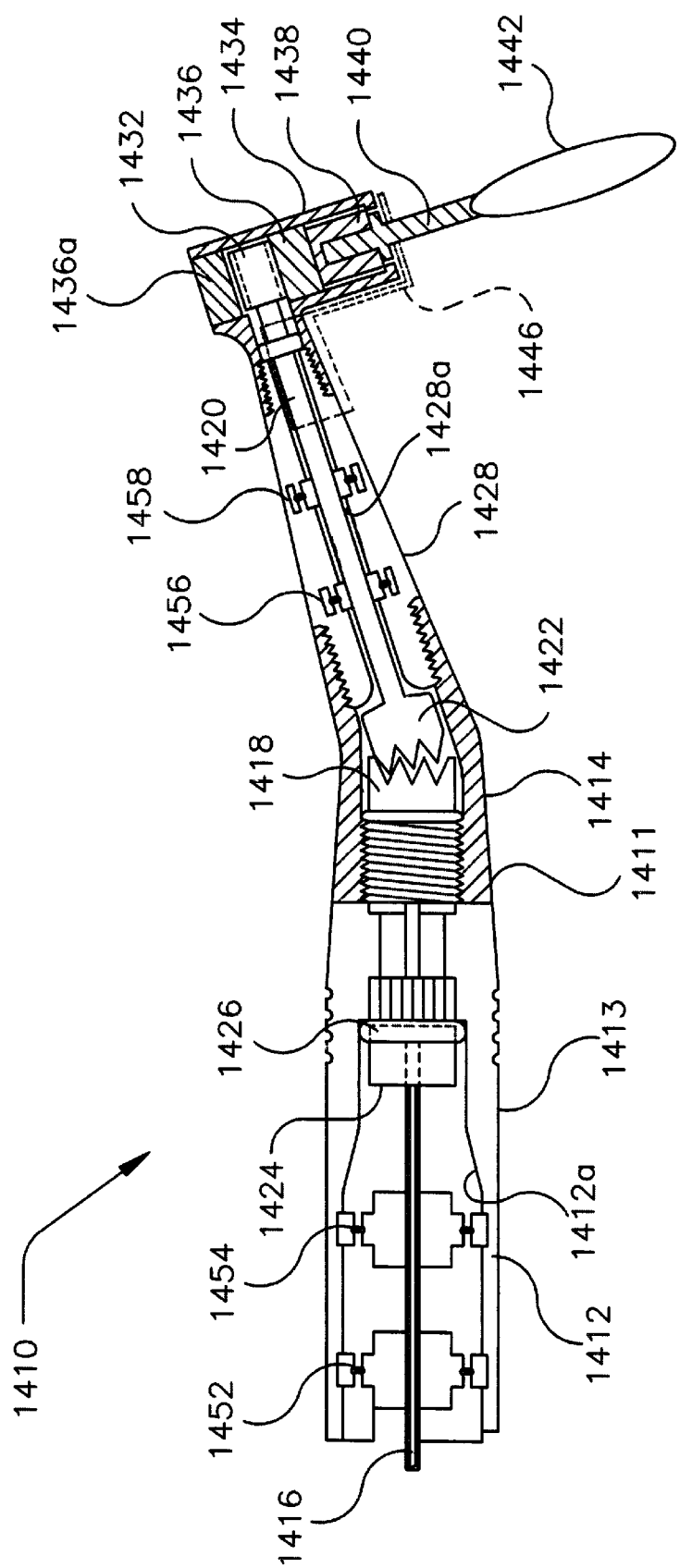
FIG. 53 is a detailed schematic of the preferred embodiment of the power periotome similar to the one illustrated in FIG. 36 with the addition of rases to reduce vibration.

FIG. 53 shows another alternative embodiment of inventive power periotome 1410. Contained within lower housing member 1412 is lower proximal race 1452 and lower distal race 1454. These races are positioned against a inside surface 1412a of lower housing member 1412 and lower rotating rod 1416, they are designed to snap into a groove in the inside wall of lower housing member 1412. The purpose of these races is to minimize vibration of lower rotating rod 1416. Contained within upper housing member 1428 is upper proximal race 1456 and upper distal race 1458. These races are positioned against inside surface 1428*a* of upper housing member 1428, and snap into a groove in inside surface 1428a. The purpose of these races is to minimize vibration of upper rotating rod 1420. The four races work collectively to reduce the vibration of power periotome 1410. In recent years there have been a lot of ergonomic research into the nerve damaging effects of repetitive vibrations, including loss of sensation in the pacinian corpuscles, meissner's corpuscles, and pain receptors, as well as damage to the microvasculature. The implementation of these races, by reducing vibration in power periotome 1410, helps to prevent such injury.

Figure 54:
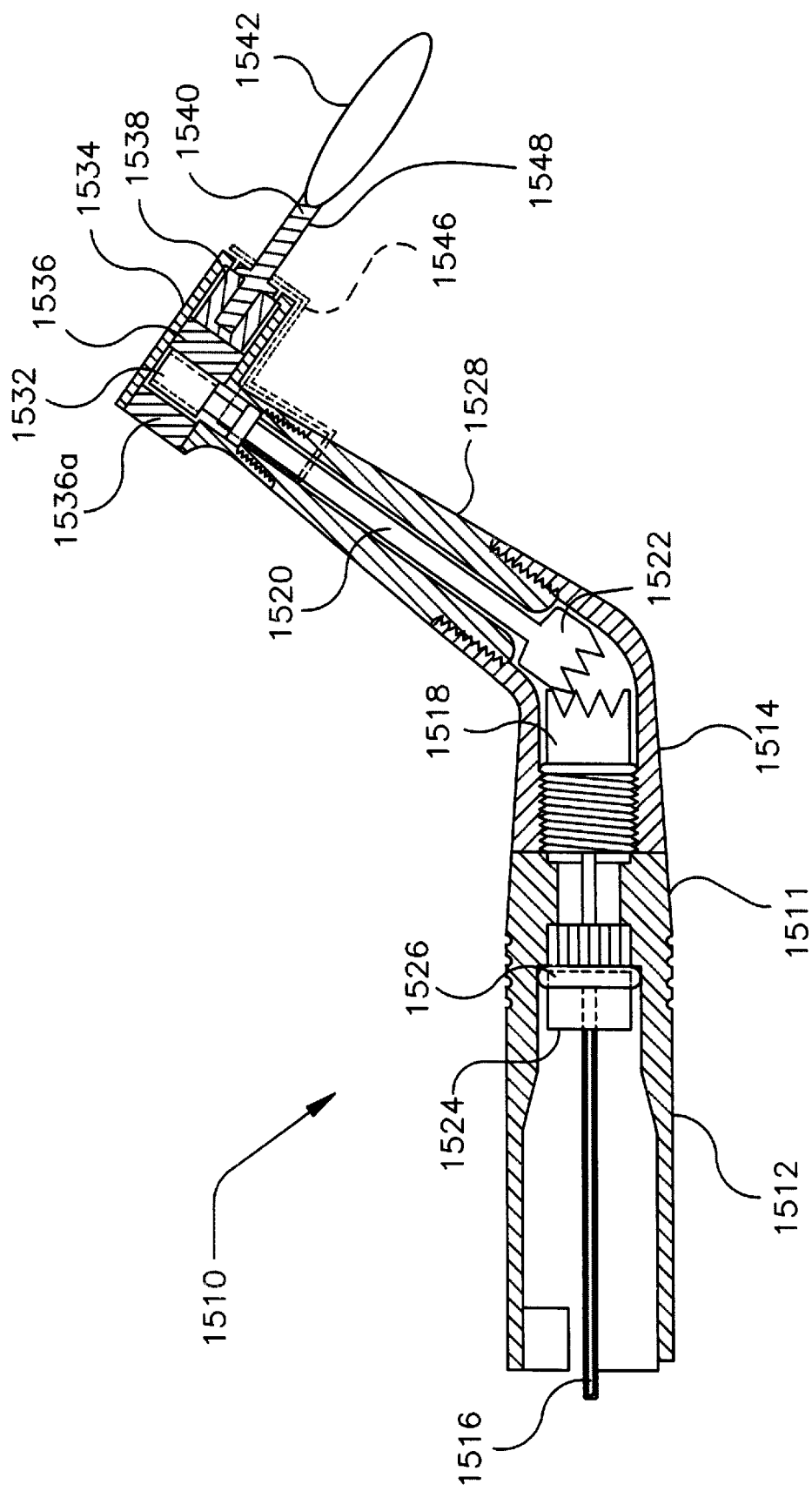
FIG. 54 is a detailed schematic of the preferred embodiment of the power periotome similar to the one illustrated in FIG. 36 with an increase in the angle between the upper housing member and lower housing member.

FIG. 54 illustrates another alternative embodiment of inventive power periotome 1510. Angled housing member 1514 positions lower housing member 1512 and upper housing member 1528 at a forty degree angle. This places blade 1548 at the relative angle to lower housing member 1512 of fifty degrees approximating the angle of the non-powered handtool currently in use. Thus giving the user the familiar feel and control he is accustomed to.

Figure 55:
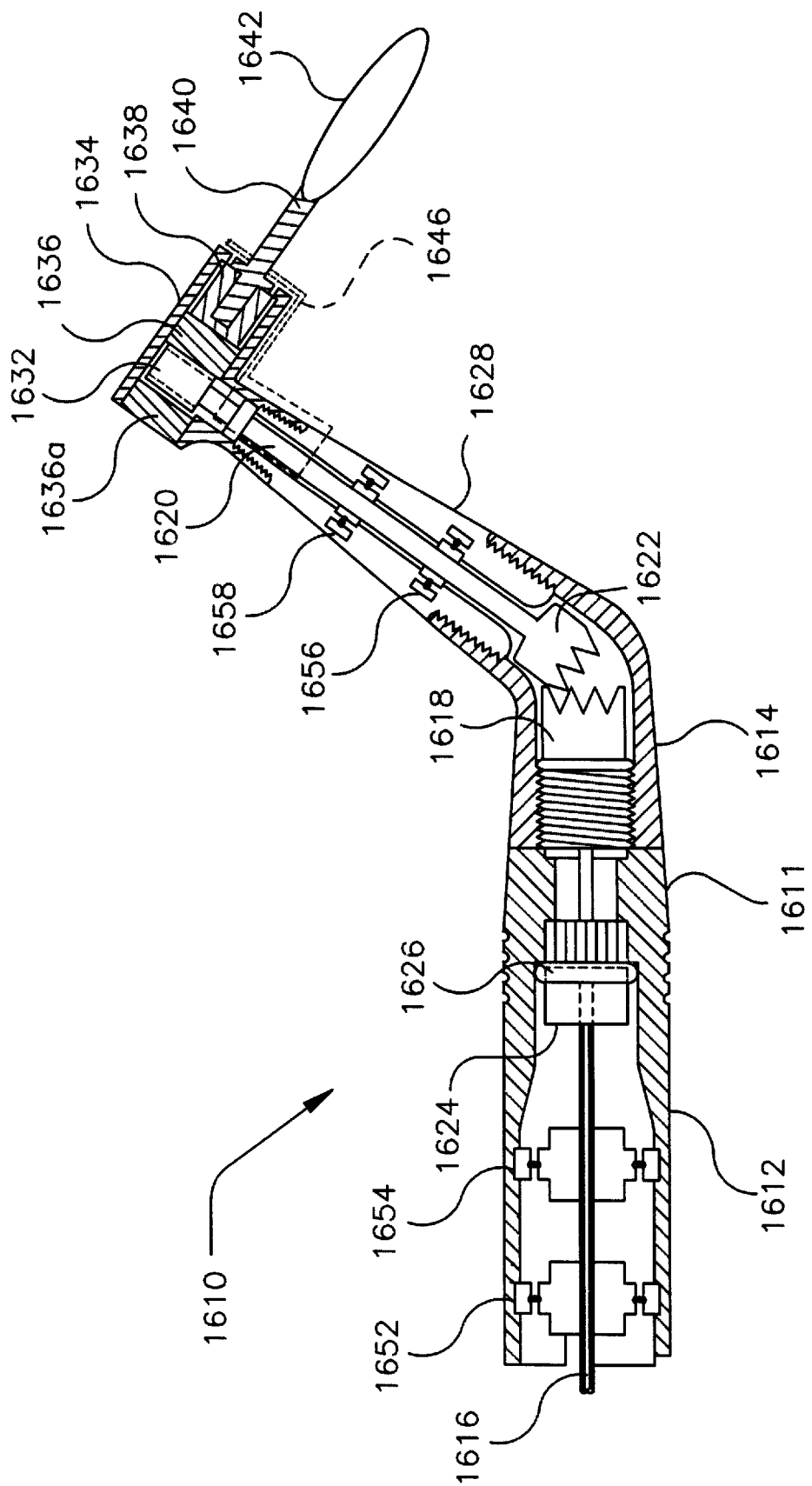
FIG. 55 is a detailed schematic of the preferred embodiment of the power periotome similar to the one illustrated in FIG. 54 with the addition of rases to reduce vibration.

FIG. 55 illustrates an alternative embodiment of inventive power periotome 1610. When angled housing 1611 is combined with lower proximal race 1652 and lower distal race 1654 upper proximal race 1656 and upper distal race 1658 to reduce the vibration as described above, this further increases the comfort and control to the user.

Figure 56:
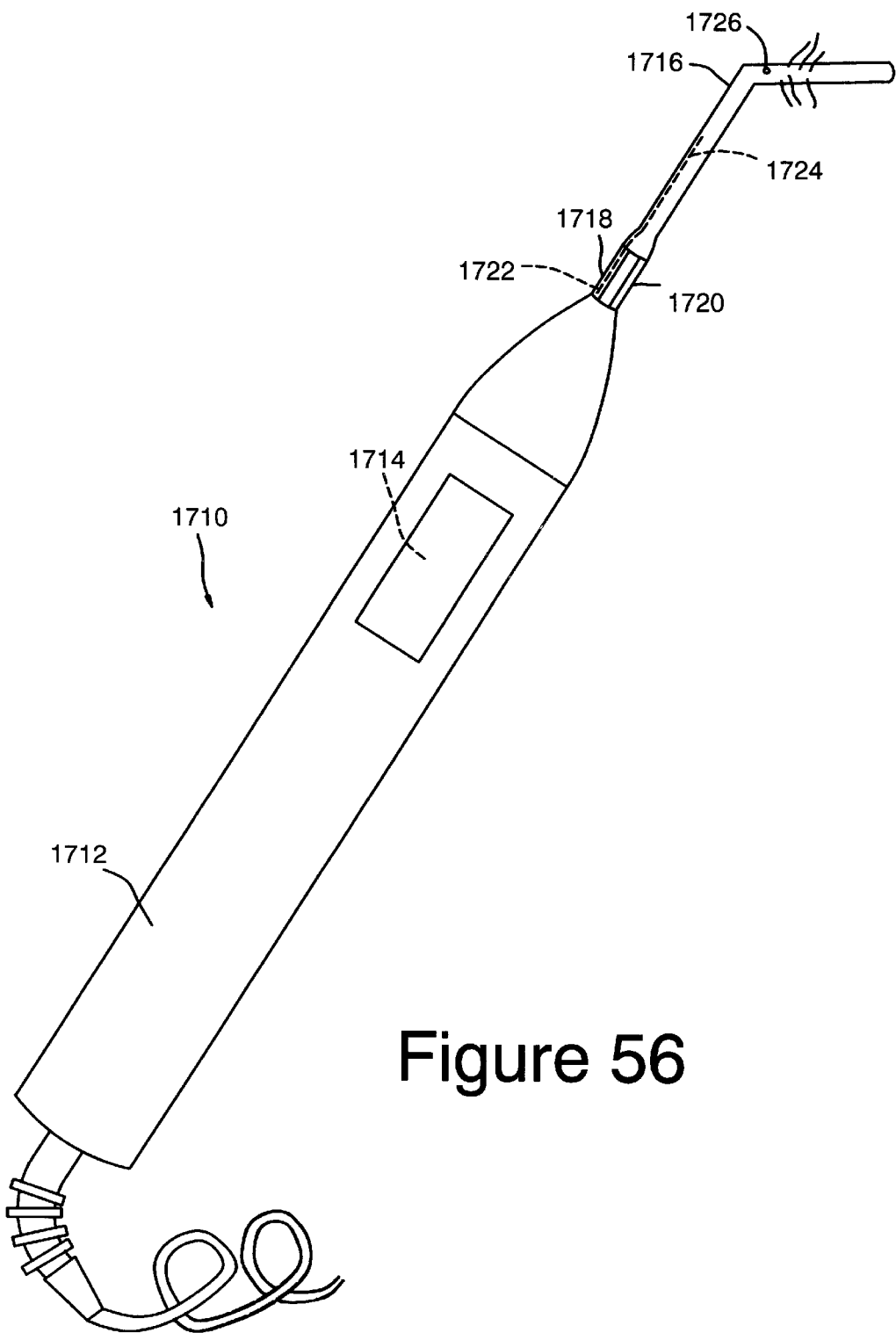
FIG. 56 illustrates a piezoelectricly powered periotome.

Referring to FIG. 56, an alternative embodiment of the inventive powered periotome is illustrated. Powered periotome 1710 comprises an electrically powered handle 1712 which encloses a piezoelectric drive mechanism 1714. Such mechanisms are well known in the dental arts, being manufactured by various companies which supply the dental field including companies in Taiwan and France. Such hand-held units are intended for plaque and tartar removal and typically drive blunt metallic instruments. In accordance with the invention, such an existing piezoelectric powered handle may be used in conjunction with a periotome bit 1716. Bit 1716 has a base 1718 comprising hex facets 1720 which allow it to be screwed onto a threaded member 1722 which extends from handle 1712.

Prior art electrically powered handle 1712 has means for irrigating a bit such as bit 1716. In accordance with the invention, an irrigation channel 1724 is provided to channel water as a coolant to a hole 1726.

Figure 57:
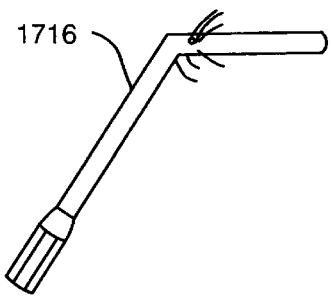
FIG. 57 illustrates a bit used in the periotome of FIG. 56.
Figure 58:
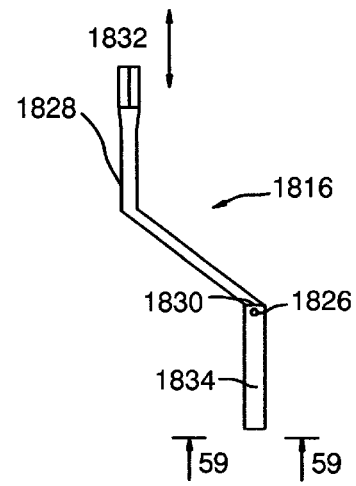
FIG. 58 illustrates an alternative bit.
Figure 60:
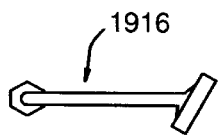
FIG. 60 illustrates an alternative embodiment of the bit of FIG. 58.
Figure 59:
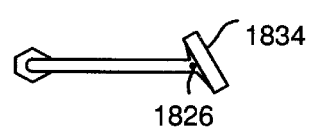
FIG. 59 is a view along lines 59—59 of FIG. 58.

Bit 1716 may be unscrewed from threaded member 1722 allowing a bit such as bit 1716 illustrated in FIG. 57 to be changed. For example, a bit particularly well-suited to work in the human mouth is illustrated FIG. 58. Bit 1816 includes a pair of bends 1828 and 1830. These ensure that the motion of the bit in the direction indicated by arrows 1832 is coupled in a most efficient and non-vibratory manner to the sharp periotome blade portion 1834 of bit 1716. As illustrated in FIG. 59, blade portion 1834 is at an oblique angle with respect to the plane defined by the remainder of bit 1816. Blade portion 1834 may also be skewed in the opposite oblique manner, as illustrated by bit 1916 in FIG. 60. Bit 1816 also includes an irrigation hole 1826.

Figure 61:
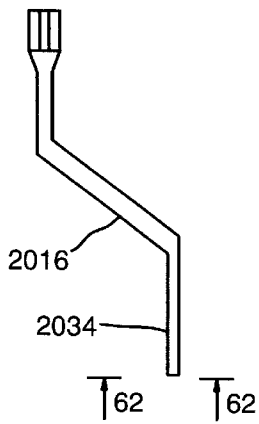
FIG. 61 illustrates another alternative bit in accordance with the present invention.
Figure 62:
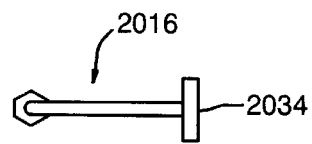
FIG. 62 is a view of the bit in FIG. 61 along lines 62—62 of FIGS. 61.

It is not necessary for the blade portion of a bit to be oblique, as illustrated by FIGS. 61 and 62 which show a bit 2016 with a blade portion 2034.

Figure 63:
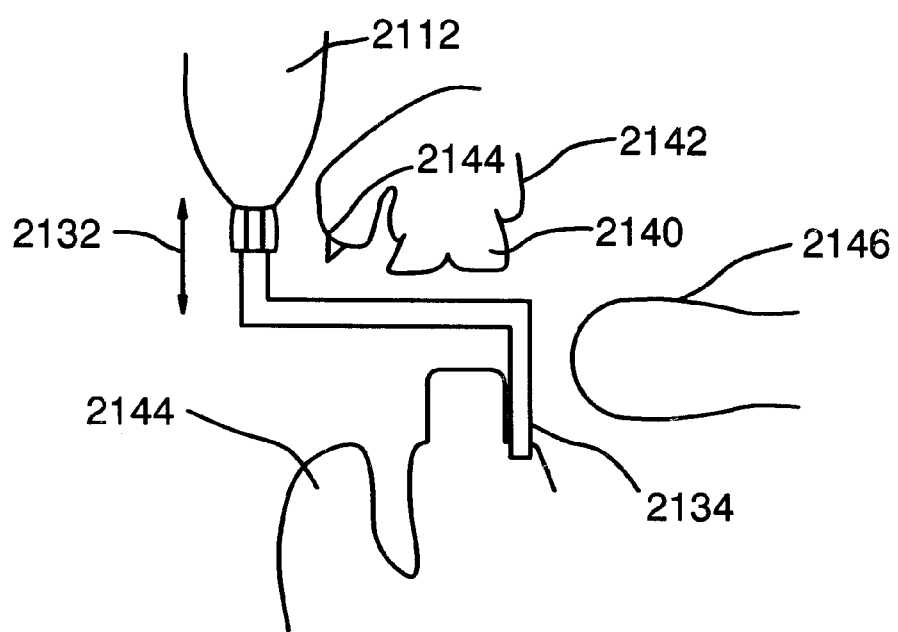
FIG. 63 illustrates the piezoelectric periotome in use.

During use of the inventive powered periotome, as illustrated in the various embodiments of FIGS. 56–62, it is contemplated that in accordance with the preferred embodiment of the inventive method of the present invention water will be used to irrigate the site, cooling the tooth and the bit. The embodiment of the invention having a pair of bends is believed to be particularly advantageous insofar as it allows motion in the direction indicated by arrow 2132 in FIG. 63 to be coupled directly to blade portion 2134 while at the same time allowing the instrument to be put into place without affecting the teeth 2140, the gums 2142, the lips 2144, or the tongue 2146.

While some illustrative embodiments of the invention have been described above, it is, of course, understood that various modifications will be apparent to those of ordinary skill in the art. Such modifications are within the spirit and scope of the invention, which is limited and defined only by the appended claims.

What is claimed is:

1. A motorized periotome for cutting into the periodontal ligaments of a patient's mouth comprising:
   a) a support member housing a motor;
   b) a dental tool, said dental tool extending from said support member and being seated in said support member such that the dental tool is capable of linear motion; and,
   c) at least one mechanical link between the motor and said dental tool in said support member, whereby the dental tool is driven in reciprocating motion, wherein said tool is manually rotatable so that it may be adjusted to be in line with the periodontal ligament space which circumscribes the tooth.

2. A motorized dental instrument as in claim 1 wherein said mechanical link comprises at least one cam, shaft and tappet coupled to each other.

3. A motorized dental instrument as in claim 2, wherein said support member further comprises a plurality of support sections, each of said support sections having an upper coupling device and a lower coupling device, whereby each of said support sections are attachable to another support section.

4. A motorized periotome as in claim 1 wherein said tool is a cutting blade configured and dimensioned for severing fibrous bony attachments.

5. A motorized dental instrument as in claim 1, wherein said motor is a piezoelectric device.

6. A motorized periotome, comprising:
   a) a support member;
   b) a dental tool, said dental tool extending from said support member and being seated in said support member such that the dental tool is capable of linear motion;
   c) a tappet seated in said support member, said tappet contacting said tool, whereby said contact extends said tool outward from said support member;
   d) at least one shaft rotatably seated in said support member, whereby said shaft is driven by said motor; and
   e) a cam coupled to said shaft, said shaft contacting said tappet wherein said tool is manually rotatable so that it may be adjusted to be in line with the periodontal ligament space which circumscribes the tooth.

7. A motorized dental instrument as in claim 6, further comprising:
   f) a second shaft rotatably seated in said support member, whereby said second shaft is driven by said motor;
   g) a first gear coupled to said second shaft;
   h) a second gear coupled to said first shaft, said first and second gears being mechanically linked.

8. A motorized dental instrument as in claim 6, further comprising:
   f) at least one ball bearing member, said member comprising a plurality of ball bearings, said ball bearing member being positioned and configured in said support member such that said shaft contacts the ball bearings as the shaft rotates.

9. A motorized dental instrument as in claim 6, wherein said support member further comprises a plurality of ball bearing members, each of said ball bearing members comprising a plurality of ball bearings and each of said ball bearing members having an upper coupling device and a lower coupling device, whereby each of said ball bearing members are attachable to another ball bearing member or said support sections.

10. A motorized dental instrument as in claim 9, wherein the upper and lower coupling devices on the support sections and the ball bearing members comprise corresponding male/female threading.

11. A motorized periotome according to claim 6 wherein said second tool comprises a triangular tipped blade.

12. A motorized periotome according to claim 11 wherein said triangular tipped blade comprises three cutting surfaces.

13. A motorized periotome according to claim 11 wherein said triangular tipped blade has a length, said length being about 25 mm.

14. A motorized periotome according to claim 6, wherein the support member and the blade form a contra angle and has a sharpened leading edge to sever the PDL fibers.

15. A motorized periotome according to claim 14, wherein the blade is about 15 mm long.

16. A motorized periotome according to claim 6 wherein said the blade is thin and flat enough to enter the periodontal ligaments space wherein the blade is flexible enough to adapt a slight curvature to conform to the root anatomy as the blade is being advanced into the periodontal ligament space.

17. A motorized periotome as in claim 6, wherein a portion of the blade is configured in a manner so the blade can be advanced deeply into the periodontal ligament space ligament space.

18. A motorized periotome for cutting into the periodontal ligaments of a patient's mouth comprising:

a) a support member;

b) a dental tool, said dental tool extending from said support member and being seated in said support member such that the dental tool is capable of linear motion;

c) a motor; and d) at least one mechanical link between the motor and said dental tool in said support member, whereby the dental tool is driven in reciprocating motion, wherein said tool is manually rotatable so that it may be adjusted to be in line with the periodontal ligament space which circumscribes the tooth.

* * * * *